United States Patent  
Salvino

Patent No.: US 12,290,245 B1  
Date of Patent: May 6, 2025

(54) OXYGEN DISPENSING LARYNGOSCOPE SLEEVE

(71) Applicant: Chris Salvino, Scottsdale, AZ (US)

(72) Inventor: Chris Salvino, Scottsdale, AZ (US)

(73) Assignee: SharpMed, LLC., Scottsdale, AZ (US)

(*) Notice: Subject to any disclaimer, the term of this patent is extended or adjusted under 35 U.S.C. 154(b) by 0 days.

(21) Appl. No.: 18/904,709

(22) Filed: Oct. 2, 2024

Related U.S. Application Data

(63) Continuation of application No. 18/904,292, filed on Oct. 2, 2024.

(60) Provisional application No. 63/632,468, filed on Apr. 10, 2024.

(51) Int. Cl.  
  *A61B 1/267* (2006.01)  
  *A61B 1/00* (2006.01)

(52) U.S. Cl.  
  CPC .......... *A61B 1/267* (2013.01); *A61B 1/00135* (2013.01)

(58) Field of Classification Search  
  CPC . A61B 1/00135; A61B 1/00142; A61B 1/267; A61M 16/0463  
  See application file for complete search history.

(56) References Cited

U.S. PATENT DOCUMENTS

| | | | |
|---|---|---|---|
| 2,821,190 A | 4/1956 | Chase | |
| 4,126,127 A * | 11/1978 | May | A61M 16/0463 600/187 |
| 4,294,235 A | 10/1981 | Storz | |
| 4,579,108 A * | 4/1986 | Bauman | A61B 1/267 600/186 |
| 6,083,151 A | 7/2000 | Renner et al. | |
| 6,843,769 B1 | 1/2005 | Gandarias | |
| 9,295,798 B2 | 3/2016 | Sartore | |
| 11,998,178 B2 | 6/2024 | Vasan et al. | |
| 2005/0059857 A1 | 3/2005 | Freier | |
| 2007/0161863 A1 | 7/2007 | Bentt | |
| 2013/0284181 A1 * | 10/2013 | Guerra | A61M 16/0463 128/207.14 |
| 2023/0210357 A1 | 7/2023 | Vasan | |

FOREIGN PATENT DOCUMENTS

| | | |
|---|---|---|
| FR | 2478458 A1 | 9/1981 |
| GB | 2477084 A | 7/2011 |

* cited by examiner

Primary Examiner — Larry E Waggle, Jr.  
(74) *Attorney, Agent, or Firm* — Kenneth Altshuler

(57) ABSTRACT

Disclosed is a laryngoscope arrangement that channels gas, such as oxygen, through a passageway and out through an exhaust port near or at a blade distal end of a laryngoscope blade of the laryngoscope to infuse a patient with the gas during an intubation procedure. The laryngoscope arrangement can either be a gas channeling laryngoscope or gas channeling sleeve that fits over a significant portion of a standard, non-gas carrying laryngoscope. In either case, the passageway is formed along a manufacturing seam of either the gas channeling laryngoscope or gas channeling sleeve. The passageway is configured to be connected to a gas source, such as a tank or compressor.

19 Claims, 20 Drawing Sheets

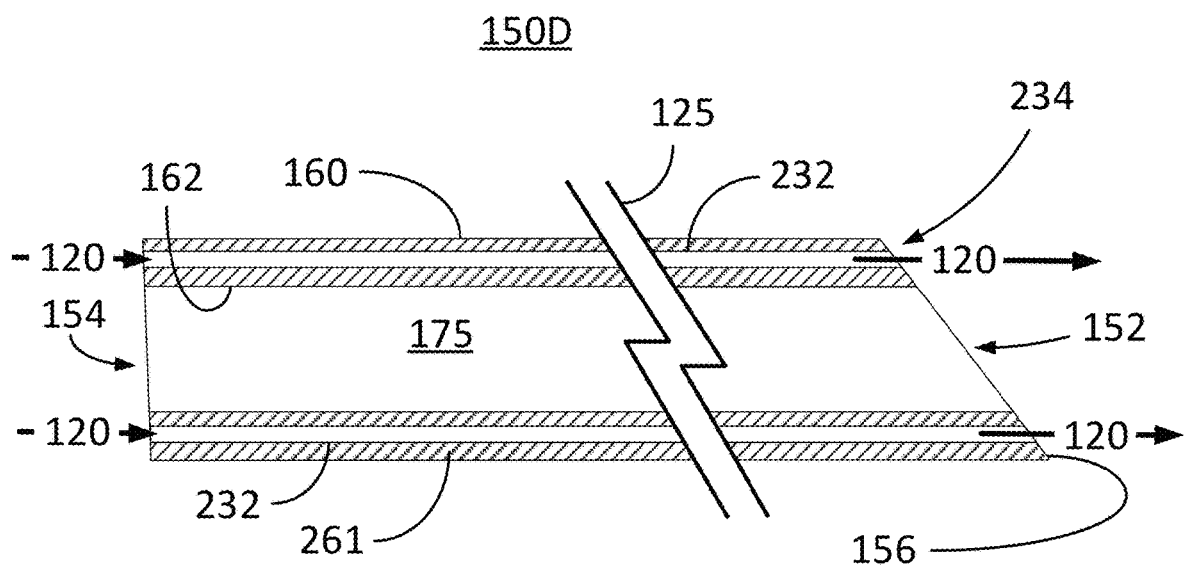
FIG. 5A
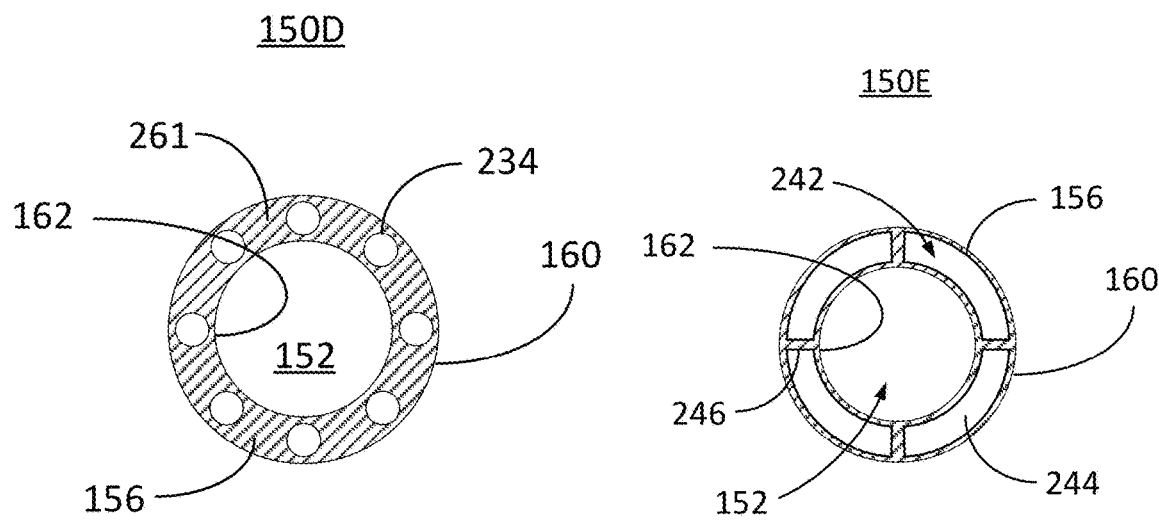
FIG. 5B  FIG. 5C

OXYGEN DISPENSING LARYNGOSCOPE SLEEVE

CROSS-REFERENCE TO RELATED APPLICATIONS

This application claims priority to and the benefit of U.S. patent application Ser. No. 18/904,292 entitled: OXYGEN DISPENSING LARYNGOSCOPE, filed on Oct. 2, 2024, which claims priority to and the benefit of U.S. Provisional Patent Application No. 63/632,468 entitled: Oxygenated Laryngoscope, filed on Apr. 10, 2024.

FIELD OF THE INVENTION

The present embodiments are directed to bougie suited oxygen dispensing laryngoscopes.

DESCRIPTION OF RELATED ART

Whether for trauma, serious illness or surgery with a general anesthetic, endotracheal tubes are a common device for providing oxygen to people in distress. An endotracheal tube, or simply ET tube, is a flexible plastic tube that threads into a person's windpipe (trachea) to assist the person in breathing. Typically, an endotracheal tube is deployed via a laryngoscope and bougie combination. Laryngoscopes comprise a lever and guide that resemble a shoehorn used to open an airway and guide a bougie or ET tube. Once deployed in a person, ET tubes connect to a ventilator to deliver oxygen to their lungs.

During an intubation procedure (where a patient is actively having an endotracheal inserted down their trachea), medical personnel sometimes have trouble positioning the end of the ET tube in the right position through a patient's vocal cords. Accordingly, excess time in deploying an ET tube jeopardizes the safety of an already oxygen deprived (not breathing) patient. Nonetheless, once the patient is intubated (the activity of having an ET tube deployed), the ET tube is connected to a ventilator which feeds oxygen to the patient.

FIG. 1 is a prior art line drawing of a commercially available laryngoscope 10. As shown, the laryngoscope 10 generally comprises a handle 16 extending between a head 14 and a blade 20. A light and possibly a camera 15 are disposed at a cutout in blade 20. The light helps illuminate a patient's airway upon entry of the blade 20. A power line (not shown) is introduced to the laryngoscope 10 via a connecting tube 12 extending from the head 14. The power line is threaded through the laryngoscope body 24 to the light and/or camera 15 to provide power to the light and/or camera 15. In practice, the caretaker will open the mouth of a person in breathing distress (patient) and insert the laryngoscope distal tip 18 through the mouth and into the upper airway to open the epiglottis so that an ET tube can be threaded into the trachea to feed the patient air.

It is to innovations related to this subject matter that the embodiments invention is generally directed.

SUMMARY OF THE INVENTION

The present embodiments are directed to oxygen dispensing laryngoscopes that are generally adapted for use with a bougie, that among other benefits improve deployment in a patient, improves oxygenation to the patient upon deployment and further improves long-term comfort.

Certain embodiments of the present invention contemplate a method for oxygenating a patient during intubation, the method comprising providing a tubular laryngoscope comprising a semirigid laryngoscope tube defined between an inlet port and outlet port. A handle is connected to the laryngoscope tube at a proximal tube region of the laryngoscope tube, the proximal tube region includes the inlet port, wherein the inlet port is in communication with an outside environment. The method further envisions a step for directing oxygen rich gas from an oxygen source in a flow direction that is through the laryngoscope tube towards the outlet port. A first portion of the oxygen rich gas flows in the flow direction through the outlet port while the laryngoscope tube is in a patient airway, and a second portion of the oxygen rich gas flows counter to the flow direction through the inlet port and into the outside environment.

Certain other embodiments of the present invention envision a laryngoscope embodiment generally comprising a laryngoscope that provides a pathway for gas, such as enriched oxygen, to be expelled from a laryngoscope blade to oxygenate a patient when being intubated. The laryngoscope embodiment can comprise a handle that extends between a head and a blade, wherein the laryngoscope has a seam where a laryngoscope left side is bonded to a laryngoscope right side. The laryngoscope further comprises a gas carrying passageway extending inside of the laryngoscope. A front seam comprises a casing that defines the gas carrying passageway, wherein prior to assembly of the laryngoscope, the laryngoscope left side comprises a first portion of the casing and the laryngoscope right side comprises a second portion of the casing, which when bonded forms the seam. The gas carrying passageway extends from an entry port located at the head to an exhaust port located at the blade.

Another embodiment of the present invention envisions a gas dispensing laryngoscope comprising a handle extending between a head and a blade with a gas carrying passageway for dispensing oxygen (or some other gas) during an intubation procedure. The gas dispensing laryngoscope defines a left side and a right side that are bonded together at a seam. The gas dispensing laryngoscope defines a blade front facing portion of the blade and a handle front facing portion of the handle, wherein the blade front facing portion is in view of the handle front facing portion. The gas carrying passageway extends inside of the gas dispensing laryngoscope along the seam at the handle front facing portion and the blade front facing portion. The gas carrying passageway extends from an entry port located at the head to an exhaust port located at the blade.

Still another embodiment of the present invention envisions a laryngoscope that channels gas during an intubation. The laryngoscope can comprise a handle extending between a head and a blade, wherein the blade has a blade front facing portion and the handle has a handle front facing portion. The blade front facing portion is in view of the handle front facing portion. The laryngoscope defines a left side and a right side that at least in part meet along a centerline at the handle front facing portion and the blade front facing portion. The laryngoscope further comprises a gas carrying passageway that extends inside of the gas dispensing laryngoscope along the centerline at the handle front facing portion and the blade front facing portion. The gas carrying passageway extends from an entry port, that is located at the head, to an exhaust port, that is located at the blade.

Another embodiment of the present invention contemplates a laryngoscope sleeve configured to cover a substantial portion of a laryngoscope, wherein the laryngoscope sleeve is configured to dispense gas, such as enriched oxygen, to a patient in need of air. The laryngoscope sleeve can comprise a sleeve handle that extends between a laryngoscope receiving aperture and a sleeve blade, wherein laryngoscope sleeve comprises a sleeve seam where a left side of the laryngoscope sleeve is bonded to a right side of the laryngoscope sleeve. A front seam is located along a blade front facing portion of the sleeve blade and a handle front facing portion of the sleeve handle, wherein the blade front facing portion is in view of the handle front facing portion. The front seam comprises a casing that defines a gas carrying passageway, wherein the left side comprises a first portion of the casing A and the right side comprises a second portion of the casing. The gas carrying passageway extends from an entry port located at the laryngoscope receiving aperture to an exhaust port located at the sleeve blade.

Still another embodiment of the present invention envisions a gas dispensing laryngoscope sleeve, comprising a sleeve handle extending between a laryngoscope receiving aperture and a sleeve blade that facilitates dispensing gas, such oxygen, to a patient in breathing distress. The gas dispensing laryngoscope sleeve defines a left side and a right side bonded together at seam. The gas dispensing laryngoscope sleeve further defines a blade front facing portion of the sleeve blade and a handle front facing portion of the sleeve handle, wherein the blade front facing portion is in view of the handle front facing portion. A gas carrying passageway extends outside of the gas dispensing laryngoscope sleeve along the seam at the handle front facing portion and the blade front facing portion from an entry port to an exhaust port located at the blade. The entry port is located at the end of a gas connecting tube approximately at the laryngoscope receiving aperture.

Another embodiment of a laryngoscope sleeve that channels gas, such as enriched oxygen, to a patient in need of air, envisions a sleeve handle extending between a laryngoscope receiving aperture and a sleeve blade with a gas emitting port. The laryngoscope sleeve defines a blade front facing portion of the sleeve blade and a handle front facing portion of the sleeve handle, wherein the blade front facing portion is in view of the handle front facing portion. The laryngoscope sleeve defines a left side and a right side that at least in part meet along a centerline at the handle front facing portion and the blade front facing portion. A gas carrying passageway extends along the centerline at the handle front facing portion and the blade front facing portion from an entry port, located at a distal end of a gas connecting tube, to an exhaust port located at the sleeve blade.

BRIEF DESCRIPTION OF THE DRAWINGS

FIG. 5A is yet another embodiment of a laryngoscope tube shown along cross-section cutline A-A consistent with embodiments of the present invention;

FIG. 5B is a front view line drawing of the distal tip of the laryngoscope tube;

FIG. 5C is a front view line drawing of the distal tip of yet another embodiment of the laryngoscope tube consistent with embodiments of the present invention;

DETAILED DESCRIPTION

Figure 1:
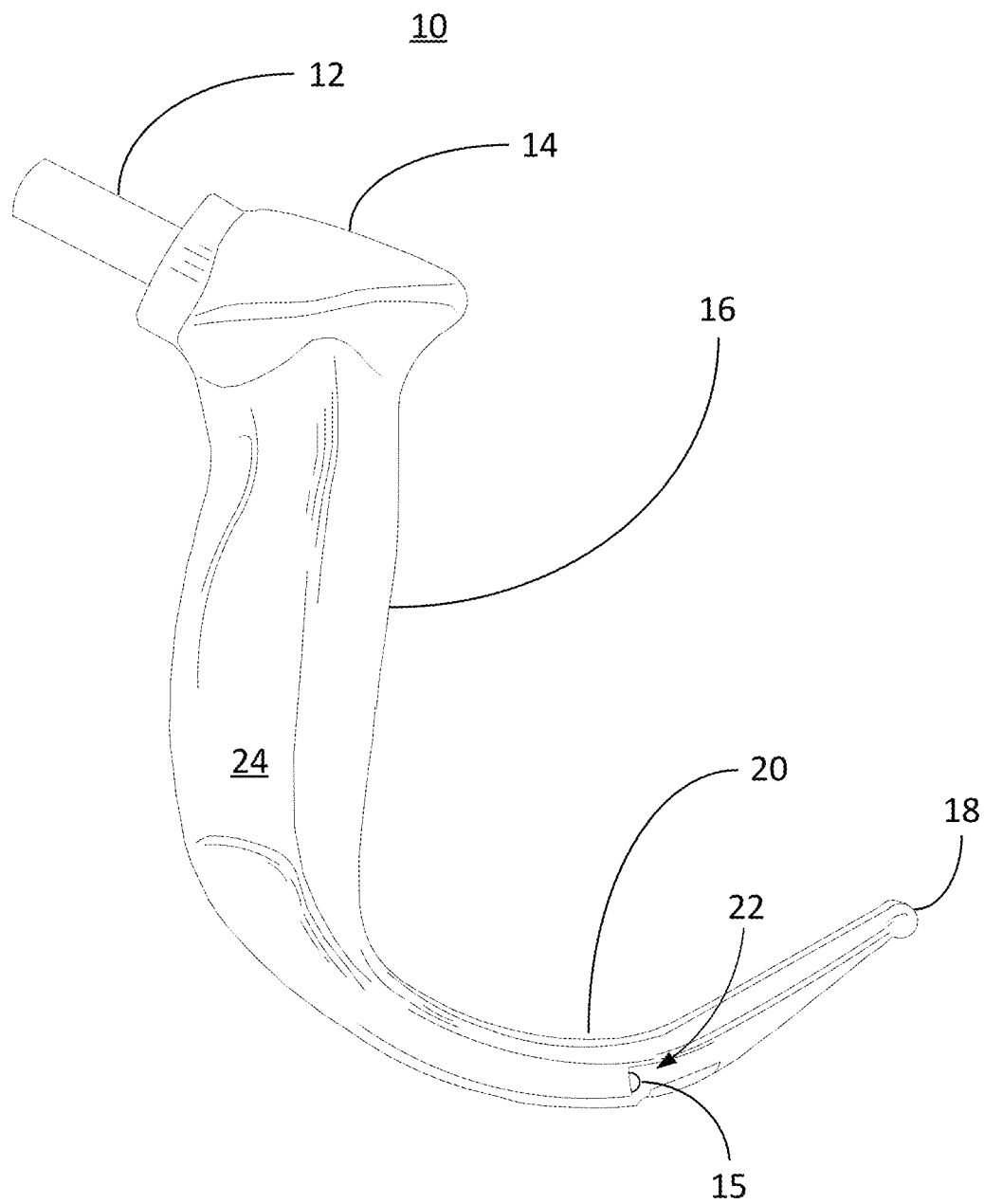
FIG. 1 is a prior art line drawing of a commercially available laryngoscope.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving the subject matter directed to the field of the invention. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phrases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical call-outs.

With respect to the drawings, it is noted that the figures are not necessarily drawn to scale and are diagrammatic in nature to illustrate features of interest. Descriptive terminology such as, for example, upper/lower, top/bottom, horizontal/vertical, left/right and the like, may be adopted with respect to the various views or conventions provided in the figures as generally understood by an onlooker for purposes of enhancing the reader's understanding and is in no way intended to be limiting. All embodiments described herein are submitted to be operational irrespective of any overall physical orientation unless specifically described otherwise, such as elements that rely on gravity to operate, for example.

Disclosed is a laryngoscope arrangement that channels gas, such as oxygen, through a passageway and out through an exhaust port near or at a blade distal end of a laryngoscope blade of the laryngoscope to infuse a patient with the gas during an intubation procedure. The laryngoscope arrangement can either be a gas channeling laryngoscope or gas channeling sleeve that fits over a significant portion of a standard, non-gas carrying laryngoscope. In either case, the passageway is formed along a manufacturing seam of either the gas channeling laryngoscope or gas channeling sleeve. The passageway is configured to be connected to a gas source, such as a tank or compressor.

Figure 2A:
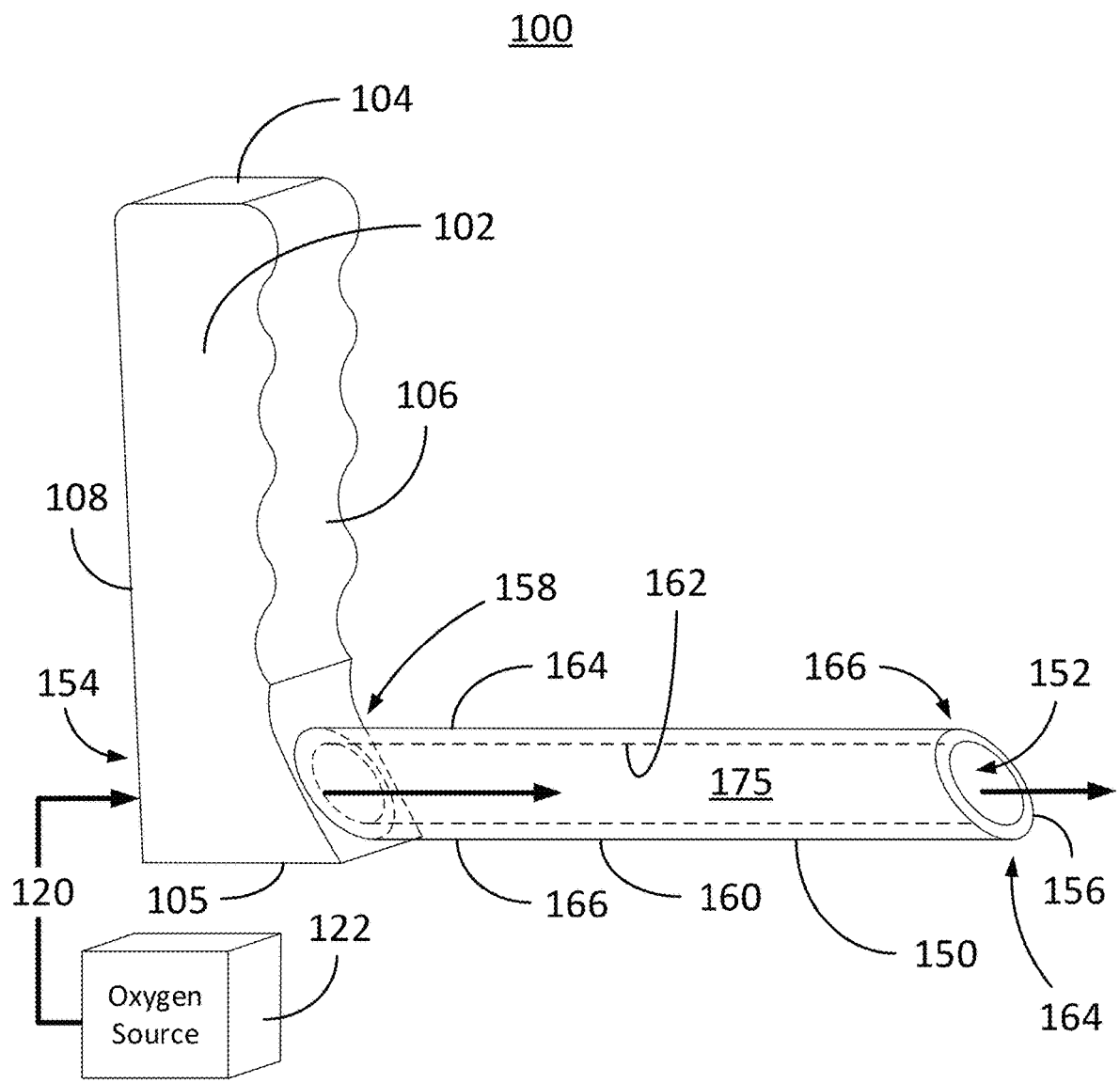
FIGS. 2A and 2B are line drawings that illustratively depict various views of a tubular laryngoscope embodiment consistent with embodiments of the present invention.
Figure 2B:
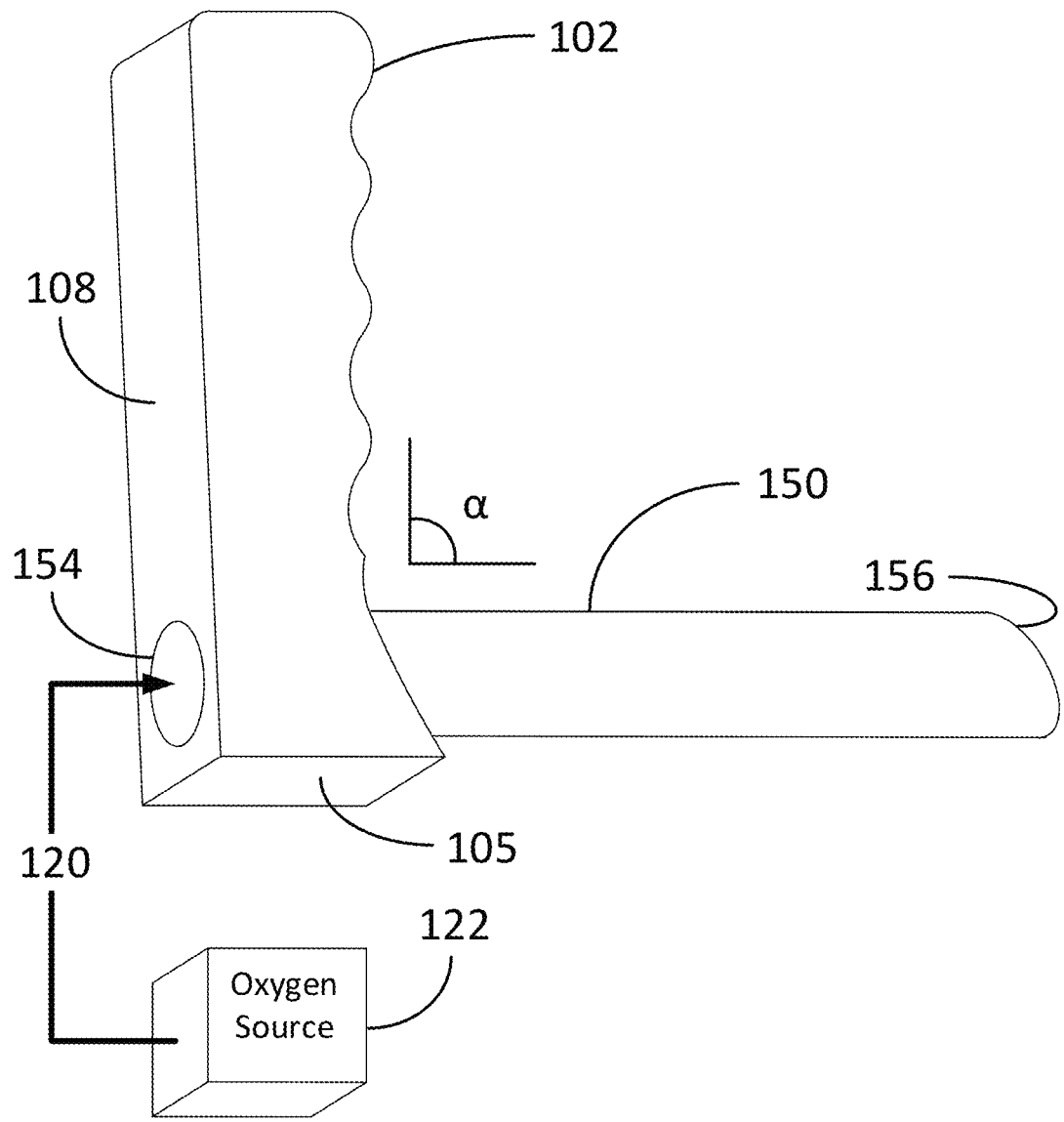
Figure 6:
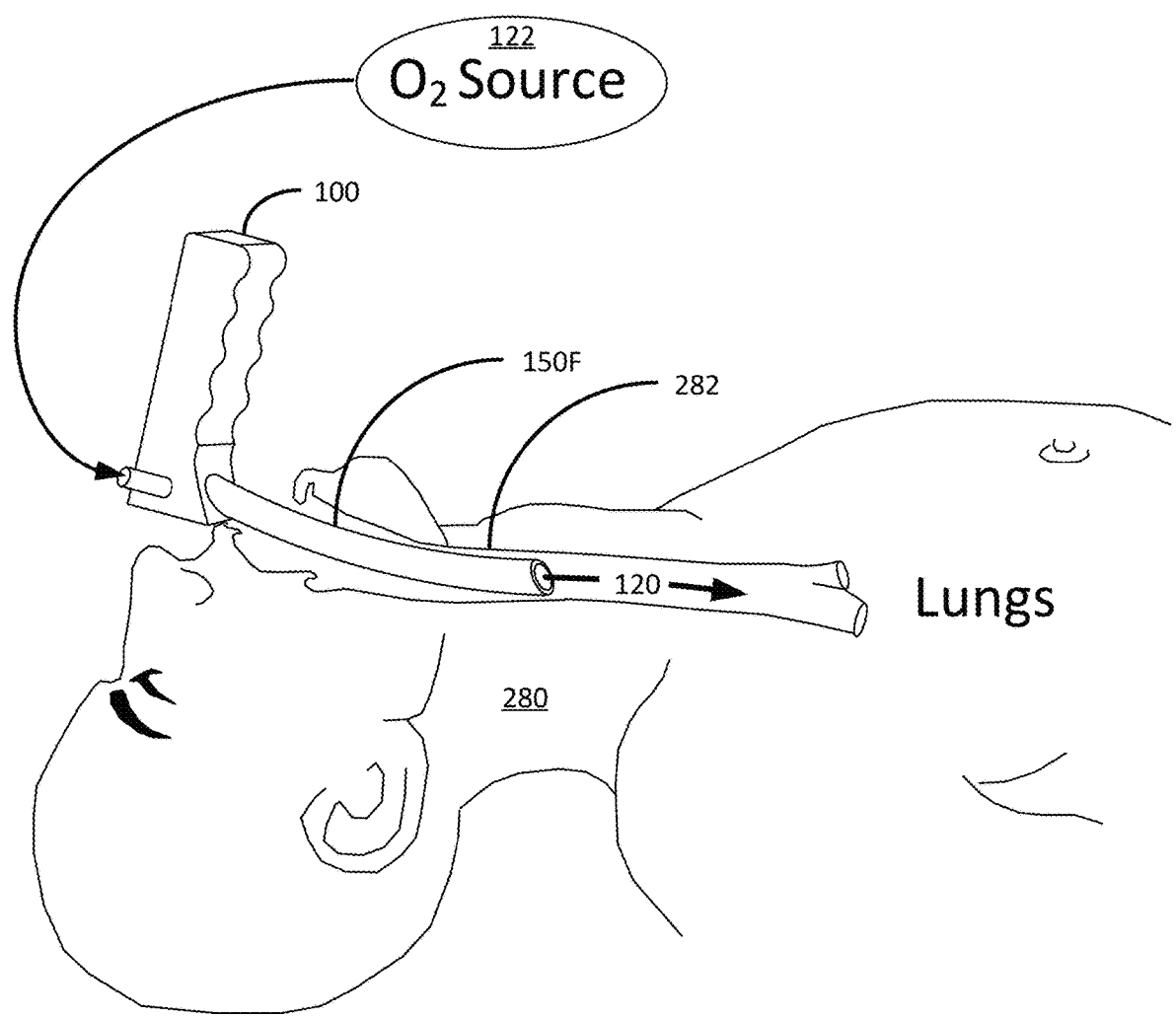
FIG. 6 illustratively depicts a patient having their airway opened with a laryngoscope embodiment, that in the present embodiment has a slightly curved laryngoscope tube.

FIGS. 2A and 2B are line drawings that illustratively depict various views of a tubular laryngoscope embodiment consistent with embodiments of the present invention. As shown in the present laryngoscope embodiment 100, a rigid laryngoscope tube 150 extends from a handle-scope end 105 of a laryngoscope handle 102 at a laryngoscope-tube-to-handle-interface 158 and terminates to a distal tip 156. The laryngoscope handle 102 is configured and arranged to be held or otherwise gripped by a human hand (not shown) that wraps around a handle back side 108 and a handle grip side 106. The laryngoscope handle 102 and the laryngoscope tube 150 form a rigid structure adapted to manhandle opening a patient's airway 282, as shown in FIG. 6. An uninterrupted pathway 175 extends at least partially through the laryngoscope tube 150 from an inlet port 154 to an outlet port 152. An oxygen source 122 provides a constant flow of oxygen 120, or in some embodiments an oxygen mixture of up to 100% oxygen, that flows through the uninterrupted pathway 175 and out from the outlet port 152 in the distal tip 156. Oxygen 120 is made to flow in the direction of the oxygen arrows 120 from the laryngoscope-tube-to-handle-interface 158 to the distal tip 156. The laryngoscope tube 150 is defined by a tube outer surface 160, a tube inner surface 162, a tube leading edge 164 and a tube trailing edge 166. Certain embodiments envision the leading edge 164 of the laryngoscope blade 150 being semi-rigid (i.e., being able to deflect a little to avoid harming the patient 280 during use of the laryngoscope 100) while the trailing edge 166 is rigid to maneuver the laryngoscope down the patient's airway 282.

FIG. 2B is a line drawing that depicts the back of the laryngoscope embodiment 100 showing the inlet port 154 that penetrates the handle back side 108. Certain embodiments envision the inlet port 154 not actually penetrating the handle back side 108, but either being the proximal end of the laryngoscope tube 150 of a portion of another element that connects to the handle 102. In this embodiment, the oxygen source 122 dispenses oxygen 120 in laryngoscope tube 150 via the inlet port 154, however, a different oxygen port leading into the laryngoscope tube 150 may be a better option because the inlet port 154 is also arranged and configured to accommodate threading a bougie guide through the pathway 175. In the present embodiment, the angle α defined between the handle 102 and the laryngoscope tube 150 is 90 degrees but other embodiments envision the angle α being between 60 degrees and 120 degrees.

Figure 2C:
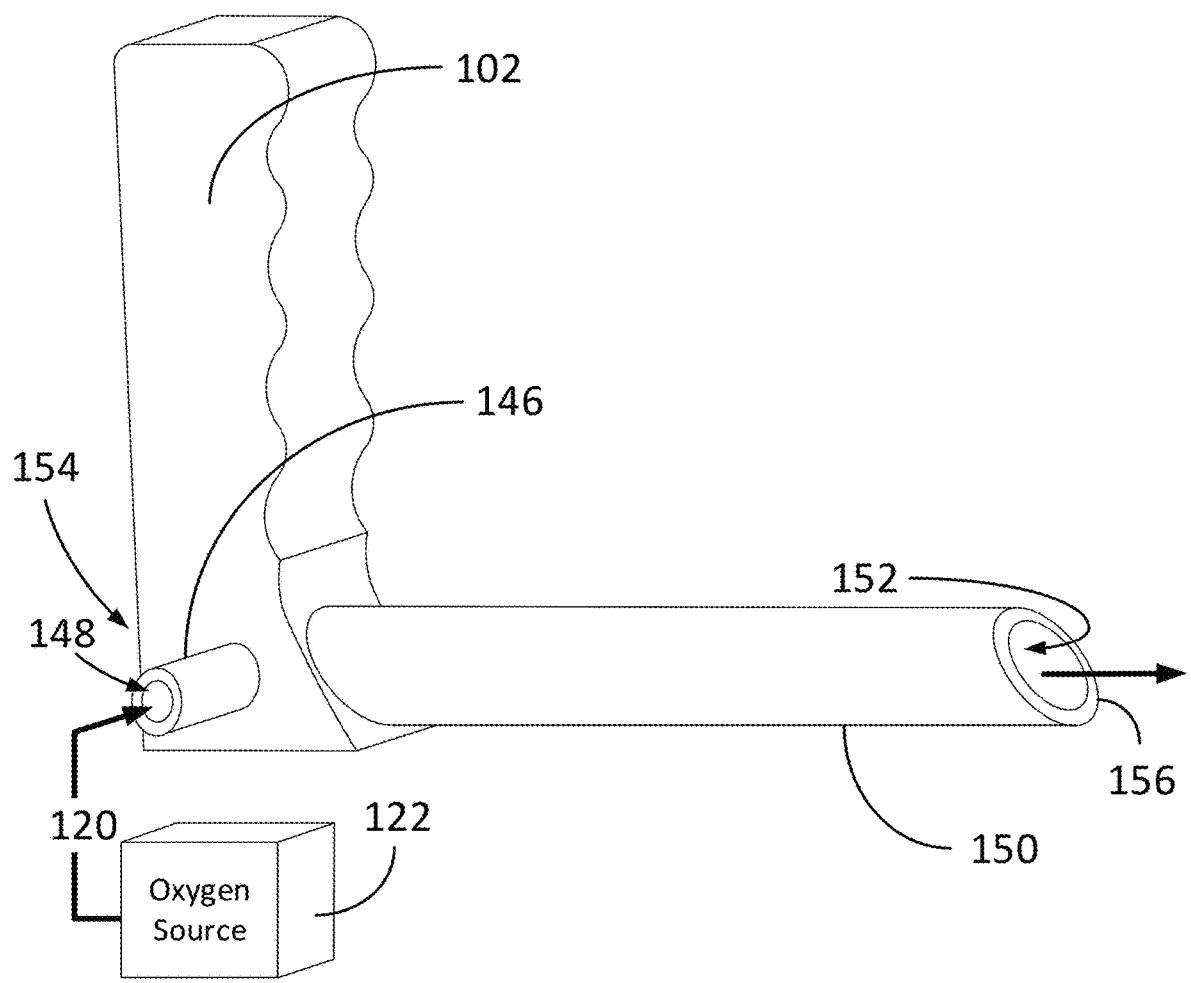
FIG. 2C is a line drawing depicting the laryngoscope embodiment with an oxygen source inlet tube extending through the handle sideways.

FIG. 2C is a line drawing depicting the laryngoscope embodiment 100 with an oxygen source inlet tube 146 extending through the handle 102 sideways. As shown, the oxygen source 122 is attached or otherwise hooked up to the oxygen source inlet tube 146 via an oxygen source tube (not shown) wherein oxygen 120 is provided to the laryngoscope tube 150 via an oxygen source inlet tube 148 at the free end of an oxygen source inlet tube 146. As with the other embodiments, oxygen 120 flows through the laryngoscope tube 150 and out the outlet port 152 at the distal tip 152. This embodiment facilitates obstructed access to the inlet port 154 to thread a bougie guide (not shown) through the inlet port 154 and out the outlet port 154. A bougie guide is a line that an operator uses to guide an ET tube (not shown) through when intubating a patient 280 of FIG. 6

Figure 2D:
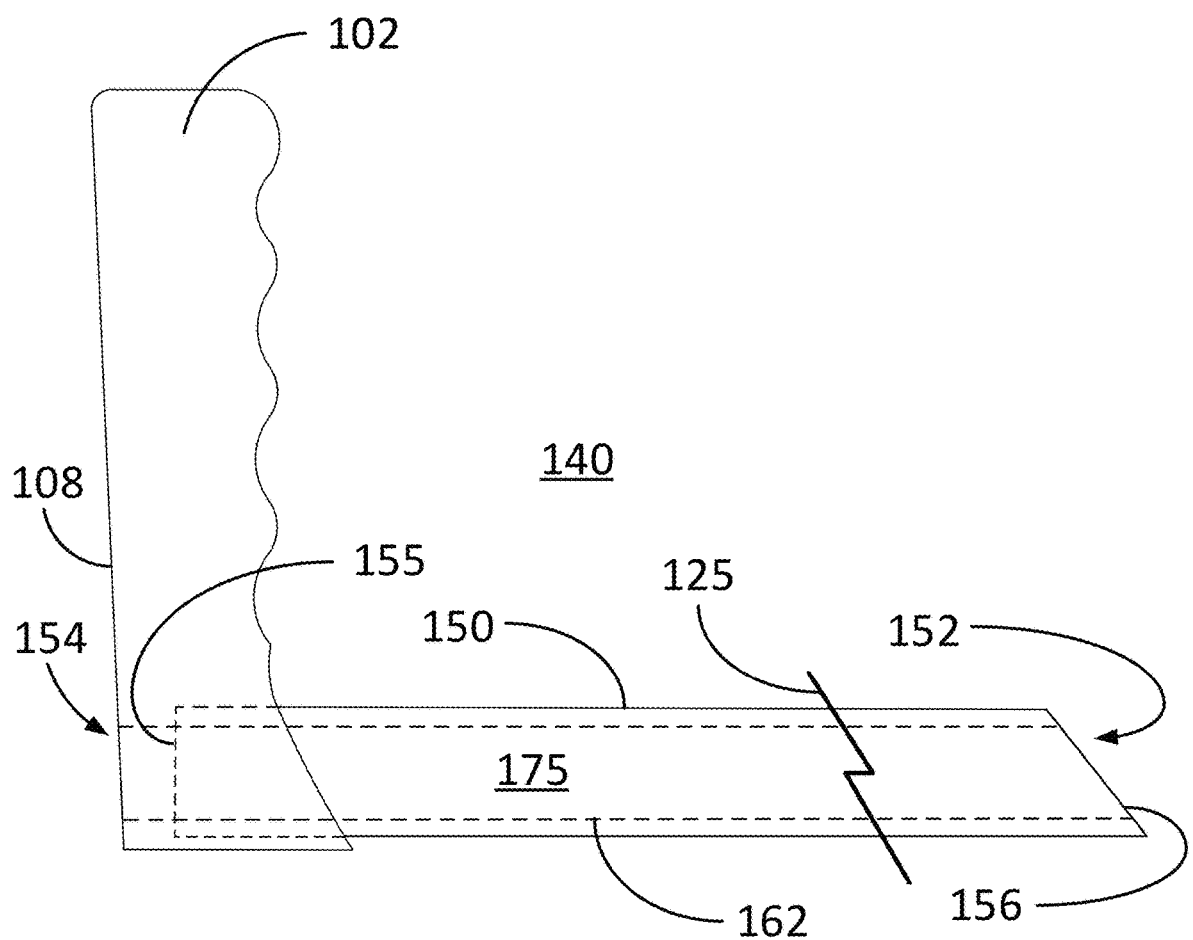
FIG. 2D is a side view line drawing of a laryngoscope embodiment consistent with embodiments of the present invention.

FIG. 2D is a side view line drawing of a laryngoscope embodiment 100B consistent with embodiments of the present invention. As shown by the hidden lines, the tube proximal end 155 of the laryngoscope tube 150 resides only partially in the handle 102, however the pathway 175 extends from the handle back side 108 to the distal tip 156. The inlet port 154 is in communication with the outlet port 152 via the uninterrupted pathway 175, which in this embodiment is a uniform, constant width along the tube inner surface 162. A break-line 125 bisects the laryngoscope tube 150 to show shorted portions of the laryngoscope tube 150.

Figure 2E:
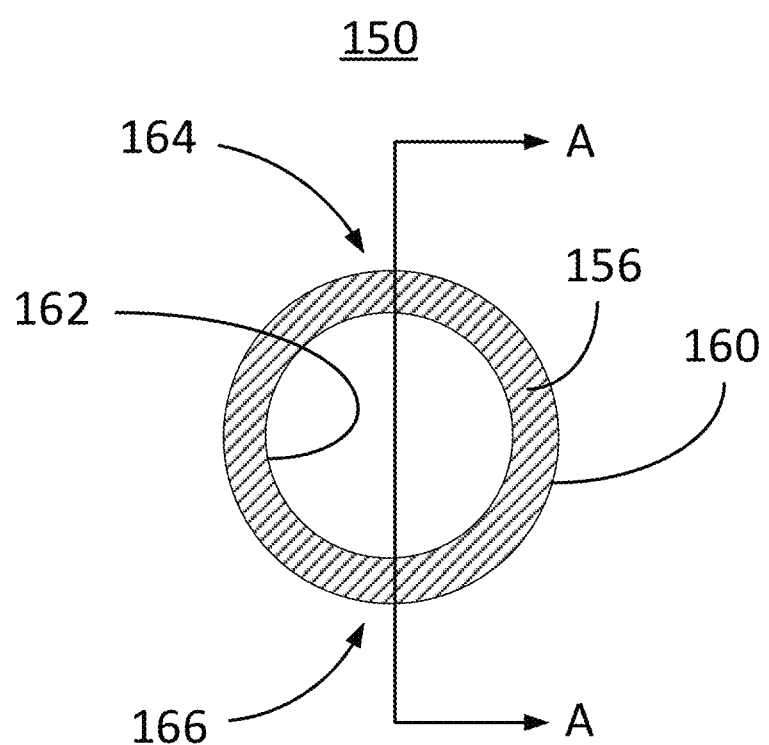
FIG. 2E is a front view line drawing of the distal tip of the laryngoscope tube with a cross-section cutline A-A bisecting the laryngoscope tube along the tube leading edge and tube trailing edge.

FIG. 2E is a front view line drawing of the distal tip 156 of the laryngoscope tube 150 with a cross-section cutline A-A bisecting the laryngoscope tube 150 along the tube leading edge 164 and tube trailing edge 166. In the present embodiment the laryngoscope tube 150 is circular with the tube inner surface 162 and tube outer surface 160 being circular, however, certain embodiments envision that the tube inner surface 162 and/or the tube outer surface 160 are not circular but some other shape, such as elliptical, box-shaped, oblong (as in a rectangle with rounded ends, such as a running track), or some other non-symmetric shape.

Figure 3A:
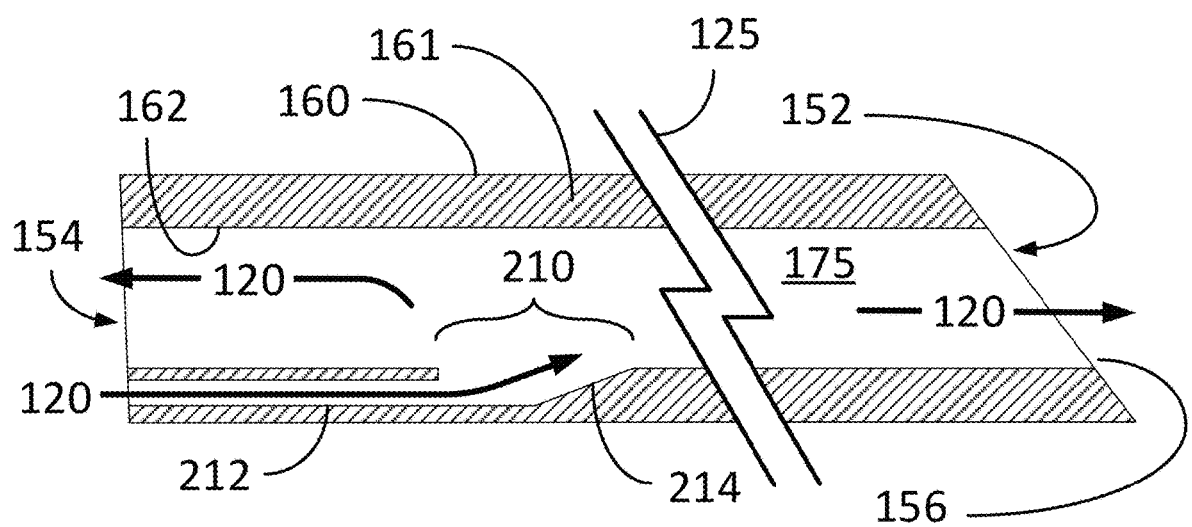
FIG. 3A is an embodiment of a laryngoscope tube shown along cutline A-A consistent with embodiments of the present invention.

FIG. 3A is an embodiment of a laryngoscope tube 150B shown along cross-section cutline A-A of FIG. 2E consistent with embodiments of the present invention. The laryngoscope tube 150B is shortened along break-line 125 to better show certain elements of interest. As shown here, the laryngoscope tube 150B has an oxygen plenum 212 that extends within the laryngoscope tube sidewall 161 between the tube outer surface 160 and the tube inner surface 162. The oxygen plenum 212 can be tubular pathway that is circular, oblong, elliptical, etc., that extends from an oxygen input, such as the oxygen source inlet tube of FIG. 1C. The oxygen plenum 212 opens up, or otherwise exits into the pathway 175 via a ramped exit port 210 inside of the laryngoscope tube 150B. In this embodiment, the flow of oxygen 120 is directed towards the distal tip 156 via the exit ramp 214 and is biased to flow out from the outlet port 152, however some of the oxygen 120 will flow out from the inlet port 154. In this way, excessive pressure from the oxygen 120 will not build up in a patent's lungs.

Figure 3B:
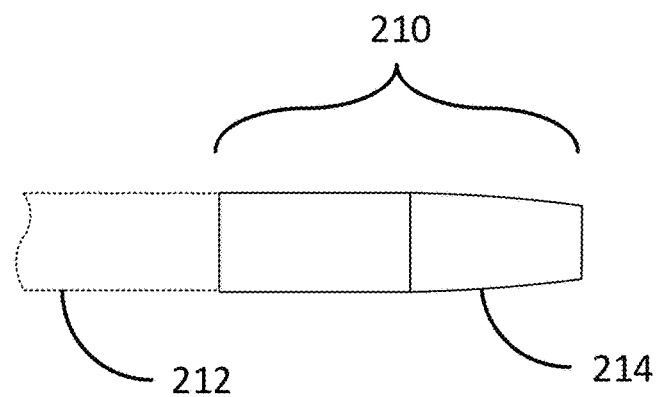
FIG. 3B is a line drawing depicting the ramped exit port of FIG. 3A.

FIG. 3B is a line drawing depicting the ramped exit port 212 of FIG. 3A. As shown, the ramped exit port 212 is viewed from inside of the pathway 175 looking down on the ramped exit port 212 (relative to FIG. 3A). The oxygen plenum 212 is shown via hidden lines because it is inside of the laryngoscope side wall.

Figure 4:
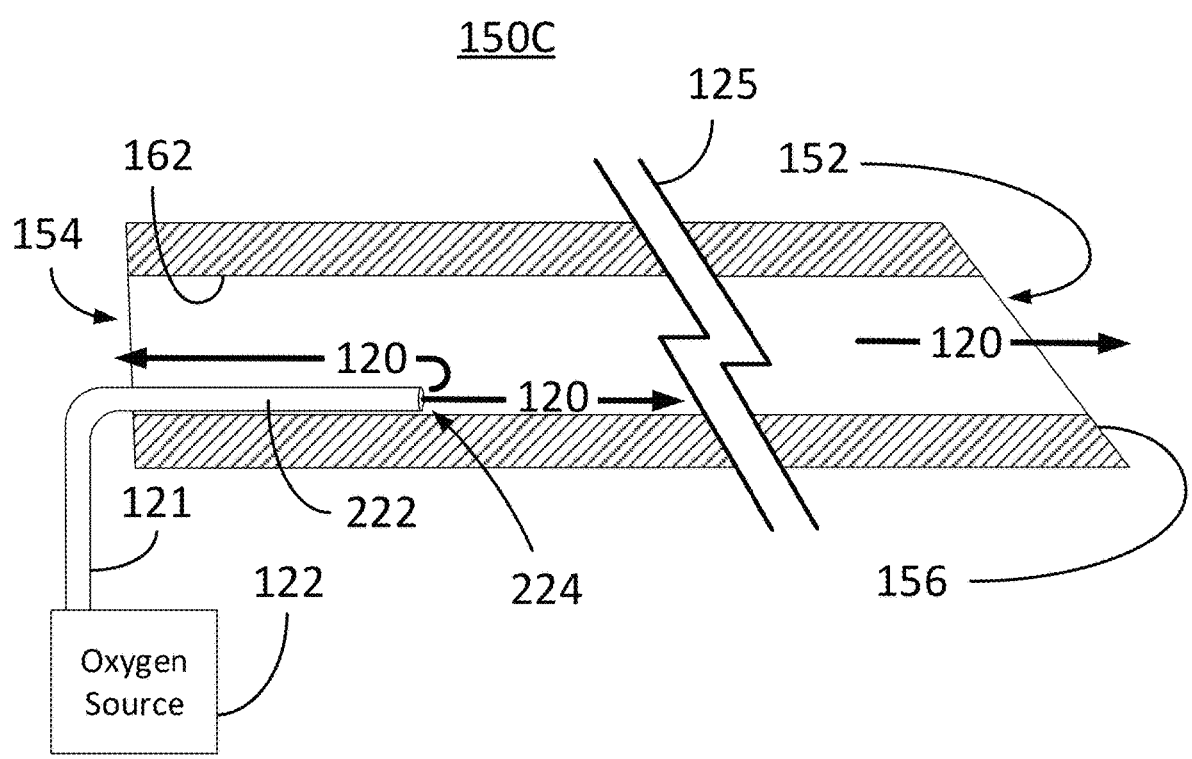
FIG. 4A is another embodiment of a laryngoscope tube shown along cross-section cutline A-A consistent with embodiments of the present invention.

FIG. 4 is another embodiment of a laryngoscope tube 150C shown along cross-section cutline A-A consistent with embodiments of the present invention. As with FIG. 3A, the laryngoscope tube 150C is shortened along break-line 125 to better show certain elements of interest. As shown here, the laryngoscope tube 150C has an internal oxygen tube 222 that runs along the tube inner surface 162 of at least part of the laryngoscope tube 150C. Oxygen 120 exits the internal oxygen tube 222, which terminates short of the distal tip 156, via the internal oxygen tube exit port 224. As illustratively depicted, oxygen 120 is directed from the internal oxygen tube exit port 224 towards the outlet port 152, however some of the oxygen 120 escapes out of the inlet port 154. Certain embodiments of the present invention contemplate the internal oxygen tube 222 extending all the way to the distal tip 156, and potentially past the distal tip 156, with internal oxygen tube exit port 224 directing oxygen 120 at or past the outlet port 152. This embodiment envisions sufficient space between the internal oxygen tube 222 and the opposing tube inner surface 162 to provide an unobstructed conduit for a bougie to be inserted through the inlet port 154 and out the outlet port 152.

FIG. 5A is yet another embodiment of a laryngoscope tube 150D shown along cross-section cutline A-A consistent with embodiments of the present invention. As with FIG. 3A, the laryngoscope tube 150D is shortened along break-line 125 to better show certain elements of interest. As shown here, the laryngoscope tube 150D comprises a plurality of oxygen pathways 232 inside of the laryngoscope side wall 261. The oxygen pathways 232 can be tubes or plenums that extend to (through) the distal tip 156. Oxygen 120 from the oxygen source 122 is introduced to the oxygen pathways 232, such as by way of an oxygen inlet tube 146. Oxygen 120 exits the oxygen pathways 232 out from the distal tip 156 via oxygen pathway exit ports 234. In this way, the pathway 175 in the laryngoscope tube 150D is unobstructed for inserting a bougie.

FIG. 5B is a front view line drawing of the distal tip 156 of the laryngoscope tube 150D. In the present embodiment the laryngoscope tube 150 is circular with the tube inner surface 162 and tube outer surface 160 being circular, however, certain embodiments envision that the tube inner surface 162 and/or the tube outer surface 160 not being circular but rather some other shape, such as elliptical, box-shaped, oblong (as in a rectangle with rounded ends, such as a running track), or some other non-symmetric shape, as discussed earlier. There is a plurality of oxygen pathway exit ports 234 distributed along the distal tip 156 in the laryngoscope side wall 261 between the tube outer surface 160 and the tube inner surface 162. Certain embodiments contemplate a single oxygen pathway 232 and corresponding oxygen pathway exit port 234.

FIG. 5C is a front view line drawing of the distal tip 156 of yet another embodiment of the laryngoscope tube 150E consistent with embodiments of the present invention. There is a plurality of oxygen channels 242 that carry oxygen 210 from the oxygen source 122 to channel exit ports 244 that open at a portion of the distal tip 156. The channels 242 are defined between the tube inner surface 162 and the tube outer surface 160 and are separated by channel separators 246, which provide spacers that separate the tube inner surface 162 from the tube outer surface 160. FIG. 5C can be the distal tip 156 view of the embodiment shown in FIG. 5A. Certain embodiments contemplate a single oxygen channel 242 and corresponding channel exit port 244.

Figure 5D:
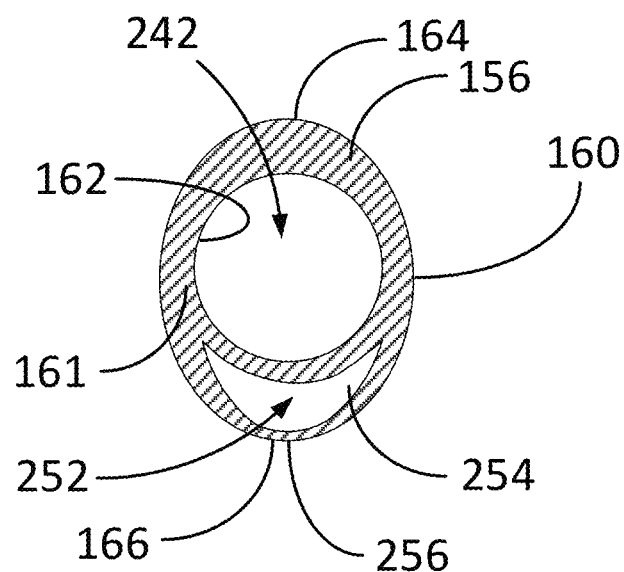
FIG. 5D is a front view line drawing of the distal tip of yet another embodiment of the laryngoscope tube consistent with embodiments of the present invention.

FIG. 5D is a front view line drawing of the distal tip 156 of yet another embodiment of the laryngoscope tube 150E consistent with embodiments of the present invention. There is one inner oxygen channel 252 that extends from where the oxygen source 222 is introduced to the laryngoscope 100 to the corresponding exit port 254. The inner oxygen channel 252 can be wider because the laryngoscope side wall 161 is thicker along the channel side 256. The channel side 256 and channel 252 can be along the leading edge 164, the trailing edge 164 or optionally 90 degrees from the leading edge 164 and trailing edge 166, assuming the elliptical shape has its longest axis sideways instead of up and down.

Certain embodiments envision channels or passageways in the laryngoscope side wall 161 being manufactured via extrusion techniques and the laryngoscope tube being a rigid clear or opaque polymer such as PVC or other suitable material known to those skilled in the art.

Figure 5E:
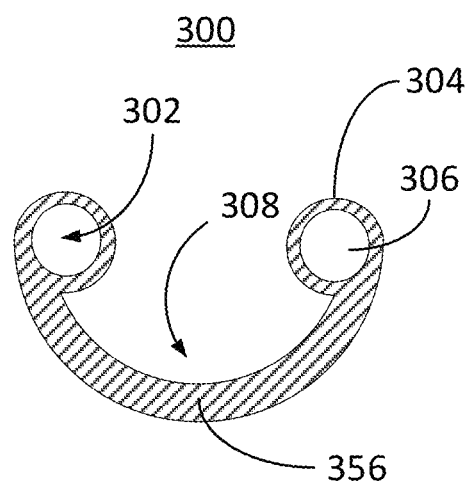
FIG. 5E illustratively depicts an optional embedded oxygen laryngoscope blade embodiment that is not tubular but rather a semicircle blade as shown by the view of the distal tip.

FIG. 5E illustratively depicts an optional embedded oxygen laryngoscope blade embodiment that is not tubular but rather a semicircle blade as shown by the view of the distal tip 265. This is more of a shoehorn laryngoscope blade 260 instead of a tube 150, wherein there is an open center channel 268 to guide an ET tube or to guide a bougie. There is at least one oxygen pathway 262 that runs along the upper blade lip 264 of the laryngoscope blade 260. The oxygen source 122 can be hooked up to an inlet port (not shown) that is in communication with an exit port 266. Like the other embodiments of the present invention, the laryngoscope blade 260 can be a rigid polymer or metal, for example and can be attached to the handle 102 in a manner like the laryngoscope tube 150. Other embodiments contemplate a blade that comprises a flat bottom or is semi rectangular or other shapes that are found in conventional laryngoscope blades but with inventive aspects of an integrated oxygen channel.

FIG. 6 illustratively depicts a patient 280 having their airway 282 opened with a laryngoscope embodiment 100, that in the present embodiment has a slightly curved laryngoscope tube 150F. The medical care provider deploys the laryngoscope embodiment 100 down the distressed patient's airway 282 while oxygen 120 from the oxygen source 122 flows to the patient's lungs. The medical care provider then either feeds an ET tube or a bougie (not shown) through the laryngoscope tube 150F. If a bougie is used, once deployed the laryngoscope 100 is withdrawn from the patient 280 and an ET tube is threaded over the bougie. Once the ET tube is in the patient, the bougie is removed and the ET tube is hooked up to a respirator (not shown).

Figure 7A:
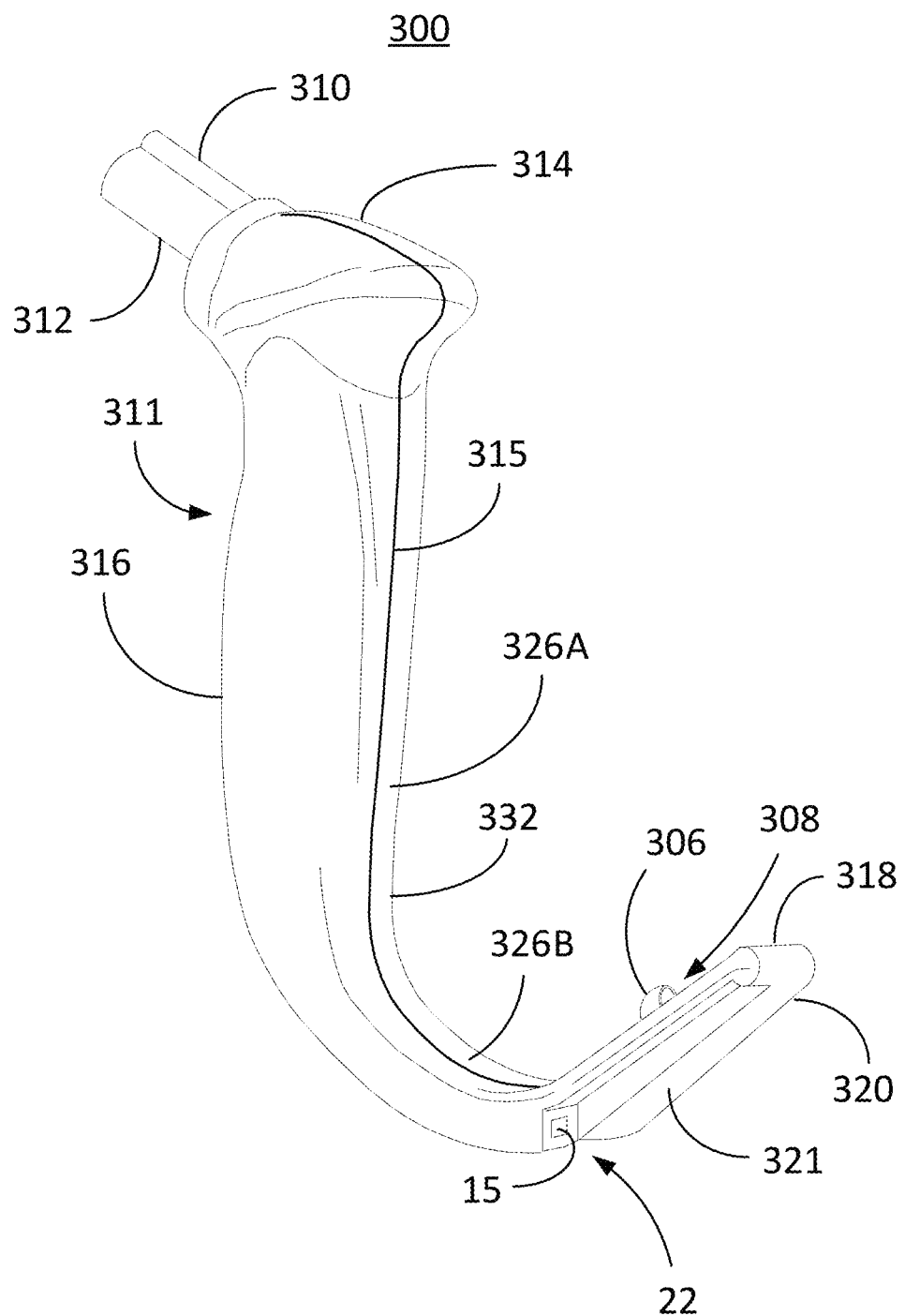
FIGS. 7A-7F are line drawings of various views of another oxygen dispensing laryngoscope embodiment consistent with embodiments of the present invention.
Figure 7B:
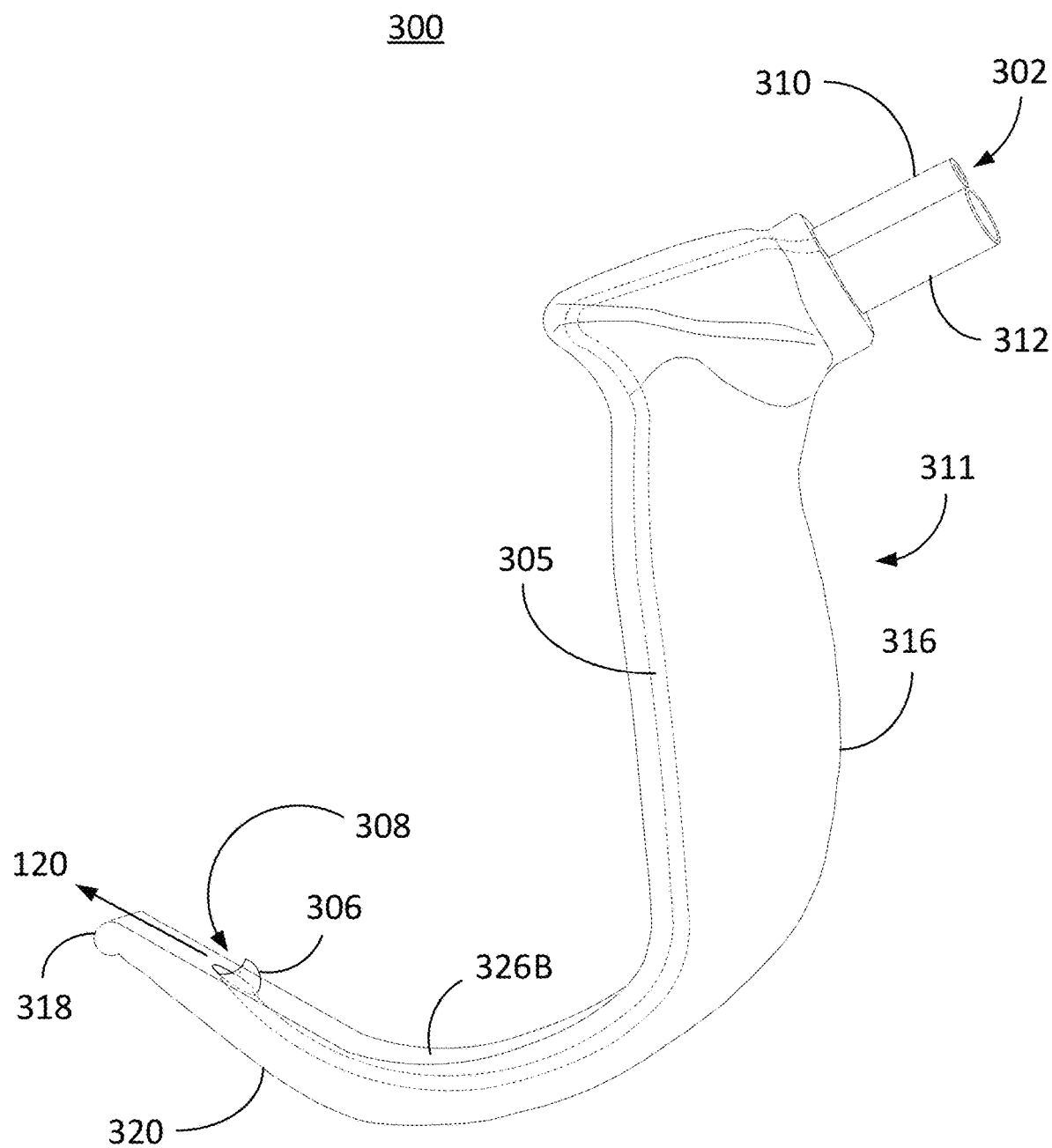
Figure 7C:
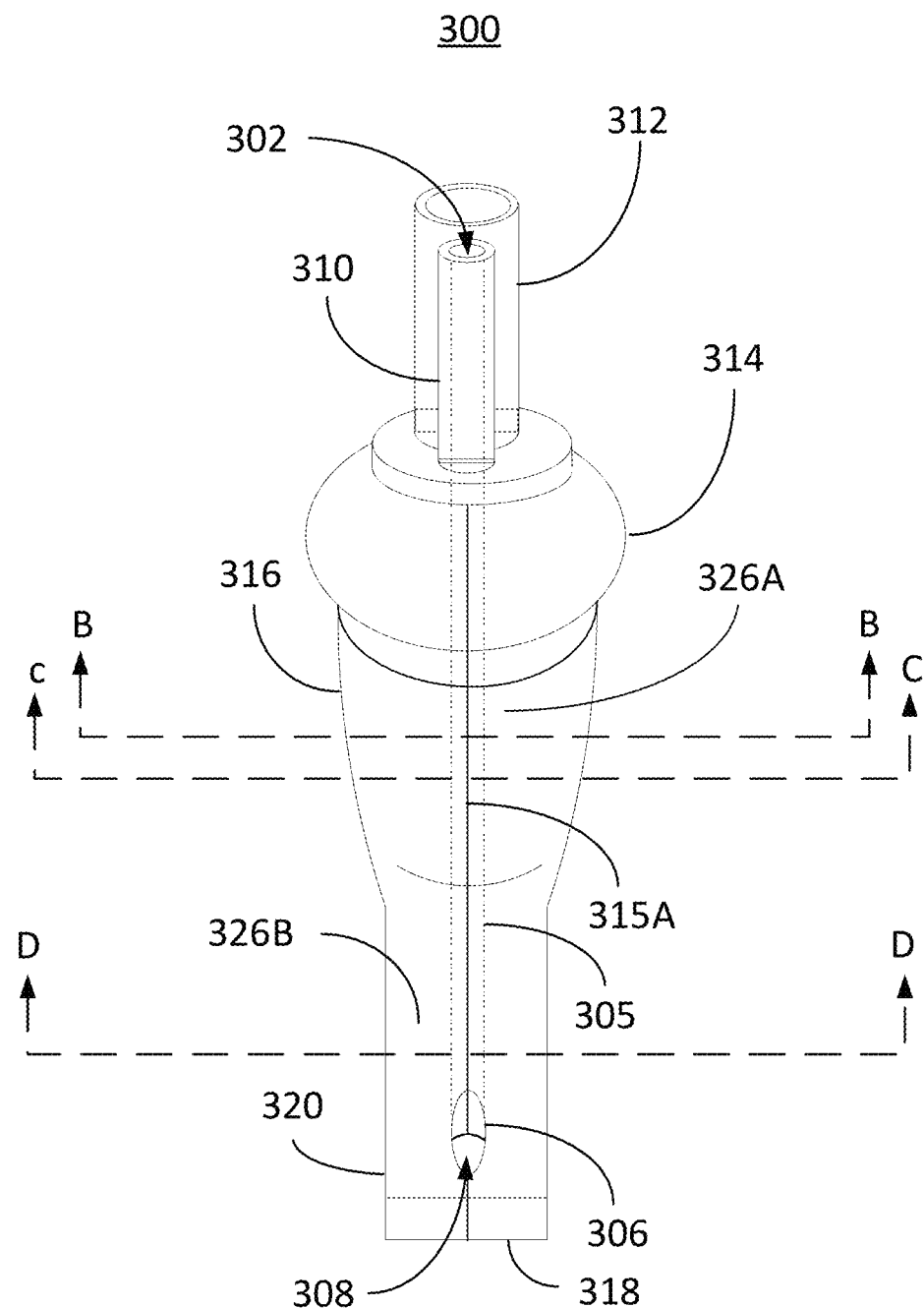
Figure 7D:
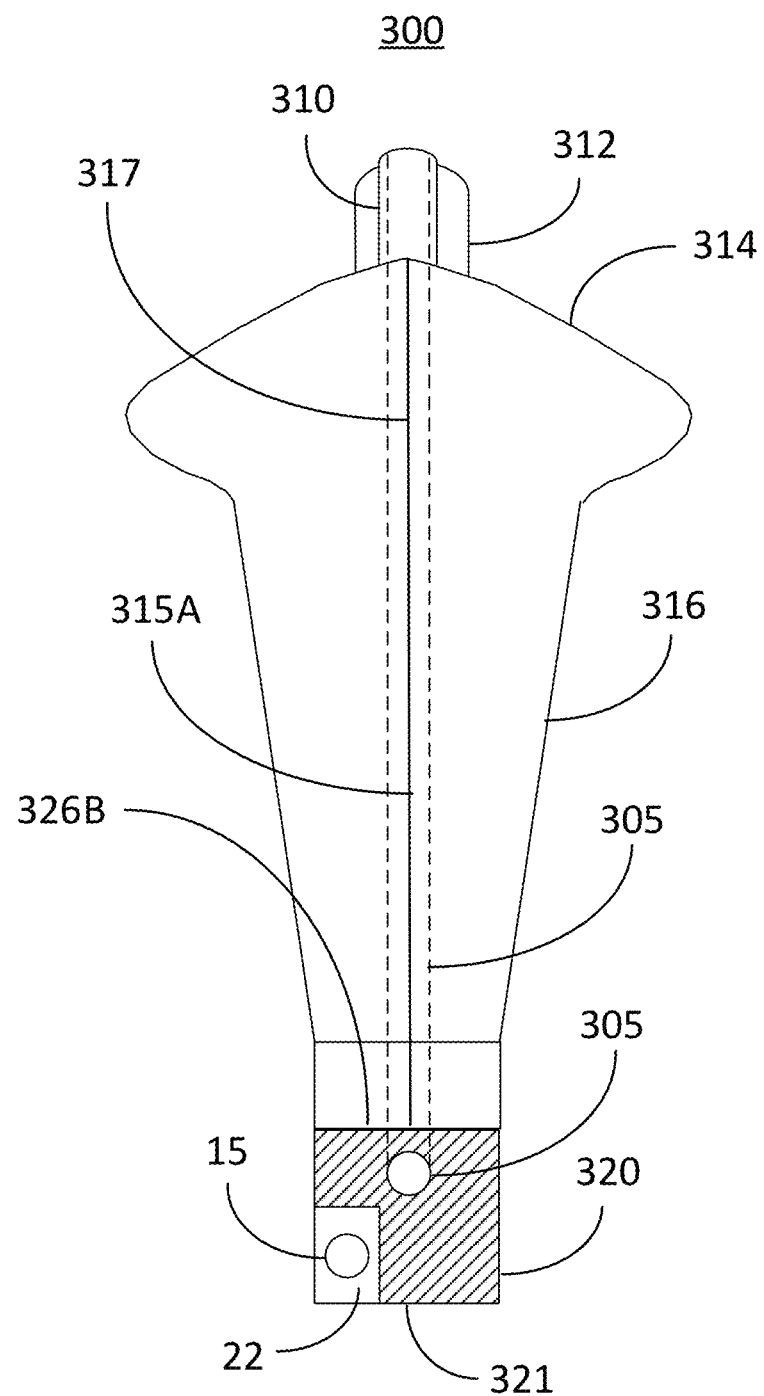
Figure 7E:
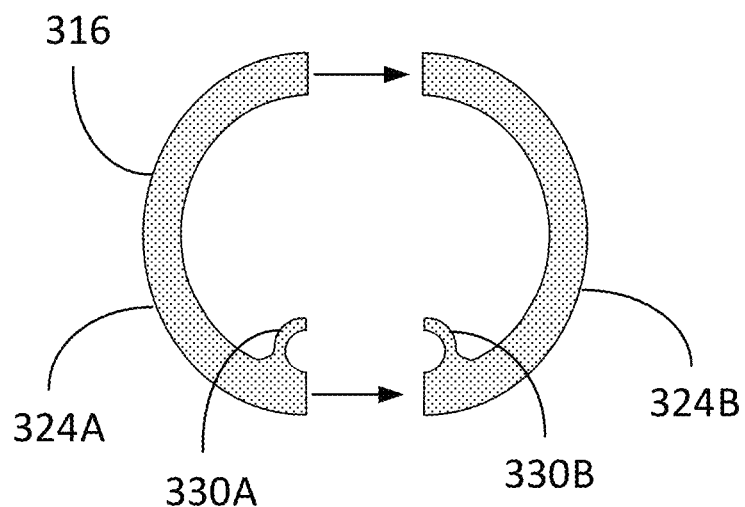
Figure 7F:
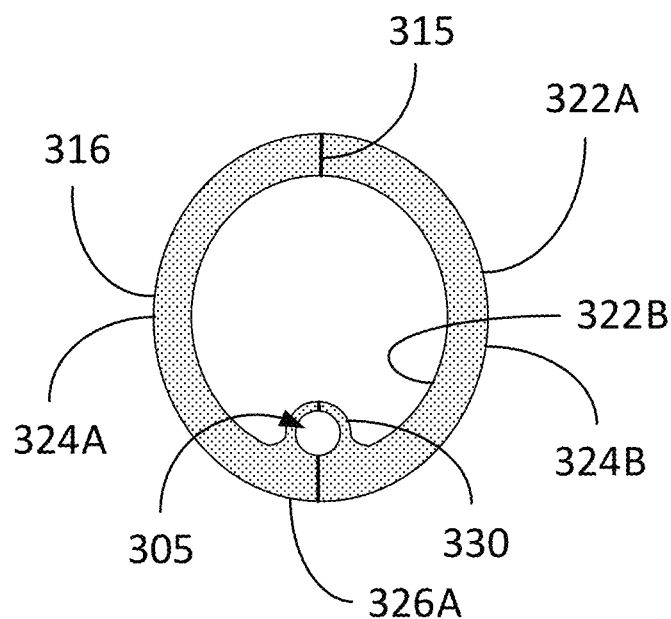

FIGS. 7A-7F are line drawings of various views of another oxygen dispensing laryngoscope embodiment consistent with embodiments of the present invention. FIG. 7A is an angled view of an oxygen dispensing laryngoscope 300 generally comprising a handle 316 that extends between a head 314 and a blade 320. In this embodiment, the blade 320 is arced in a concave shape with the blade front facing portion 326B facing the handle front facing portion 326A. The handle 316 is meant to be grasped by a human hand, wherein the head 314 is sized and shaped for a user's thumb and forefinger to lock against the laryngoscope 300. As shown here, the laryngoscope 300 comprises a seam 315 formed by a manufacturing process (a manufacturing seam which is a residual artifact of a molding manufacturing process) where a left side 324A of the laryngoscope 300 is bonded to a right side 324B of the laryngoscope 300, as shown in FIGS. 7E and 7F. In this embodiment, a light and/or camera supporting access tube 312 extends away from the back side 311 of the head 314, as shown. The camera/light connecting tube 312 is an access tube for a fiber optic, a camera, or optionally an electrical line that supplies power and communication to a light and/or camera 15, which in this embodiment is disposed at a termination location 22 in a recess in the bottom 321 of the blade 320. The fiber optic, camera, or electrical line can be threaded through the head 314, handle 316 to the camera/light termination location 22. The light illuminates the patient's trachea upon deployment of the laryngoscope 300 and a camera provides a view on a monitor of the patient's trachea upon deployment of the laryngoscope 300. A gas carrying passageway 305 extends inside of the laryngoscope 300 is in fluid communication with a gas entry port 302 in a gas connecting tube 310 extends from the head 314 in the same direction as the light/camera connecting tube 312. It should be appreciated that the gas connecting tube 310 can be located or otherwise extend elsewhere from the laryngoscope 300 without departing from the scope and spirit of the present invention. The gas carrying passageway 305 extends from the entry port 302 to an exhaust port 308 located at the blade 320. In this embodiment, the exhaust port 308 extends through an exhaust port hood 306 located between the blade distal tip/end 318 and where the blade 320 meets the handle 316.

FIG. 7B is essentially a side view of the laryngoscope 300 with a slight bias towards the back side 311 of the laryngoscope 300 to present the blade front facing portion 326B. As shown, air 120 (such as oxygenated rich gas) is made to flow from the entry port 302 in the gas connecting tube 310, through the gas carrying passageway 305 and out from the exhaust port 308 at the exhaust port hood 306. The airflow 120 is expelled from the exhaust port 308 in the exhaust port hood 306 is directed over the blade distal end 318 down a patient's airway 282.

FIG. 7C is a front view of the laryngoscope 300 looking down on the blade 320. The light/camera connecting tube 312 and gas connecting tube 310 are shown extending from the head 314. The gas carrying passageway 305, depicted by dashed lines, extends from the entry port 302 to the exhaust port 308 in the exhaust port hood 306 between the distal end 318 and where the blade 320 connects to the handle 316. The front seam 315A is shown running along the head 314, the handle front facing portion 326A and the blade front facing portion 326B. There is a cross-section cutline D-D slicing through the blade 320 proximally from the exhaust port 308. There are also two cross-section cutlines B-B and C-C slicing through the handle 316.

FIG. 7D illustratively depicts a front view of the laryngoscope 300 showing the cross-section D-D of the gas carrying passageway 305 in the blade 320. The cutline D-D is right in front of the light and/or camera 15 showing the recess of the camera/light termination location 22 at the bottom left-hand side of the blade 321. The front seam 315A is depicted extending along the head 514, along the handle 316 and blade front facing portion 326B. The front seam 315A is also along the centerline 317 of the laryngoscope 300. The dashed lines represent the gas carrying passageway 305 extending through the laryngoscope 300 from the gas connecting tube 310 (just in front of the light/camera connecting tube 312) to the cross-section D-D.

FIGS. 7E and 7F illustratively depict a hollow handle embodiment between the cross-section cutlines B-B and C-C consistent with embodiments of the present invention. Another embodiment of the laryngoscope contemplates the handle 316, head 314 and blade 320 being solid. As shown in FIG. 7E, one manufacturing method contemplates a first mold (typically a polymer, such as a rigid PCV, for example) of the laryngoscope left side 324A positioned to be connected to a laryngoscope right side 324B, as shown by the arrows. In this embodiment, the gas carrying passageway 305 is formed by a first casing portion 330A to the left and a second casing portion 330B to the right. FIG. 7F illustratively depicts the cross-section of the handle 316 between the cross-section cutlines B-B and C-C. As shown, the laryngoscope left side 324A is connected to a laryngoscope right side 324B with the casing 330 defining the gas carrying passageway 305. The casing 330 essentially places the gas carrying passageway 305 along the handle inner surface 322B along the handle front facing portion 326A. The laryngoscope left side 324A can be connected to the laryngoscope right side 324B via methods known to those skilled in the art, such as a sonic weld process, heat staking process, glue, bolt, just to name several examples. Other embodiments envision the casing 330 residing along the handle outer surface 322A or somewhere between the handle inner surface 322B and the handle outer surface 322A. The seam 315 where the laryngoscope left side 324A and the laryngoscope right side 324B connect is prominently shown by the line.

Figure 8:
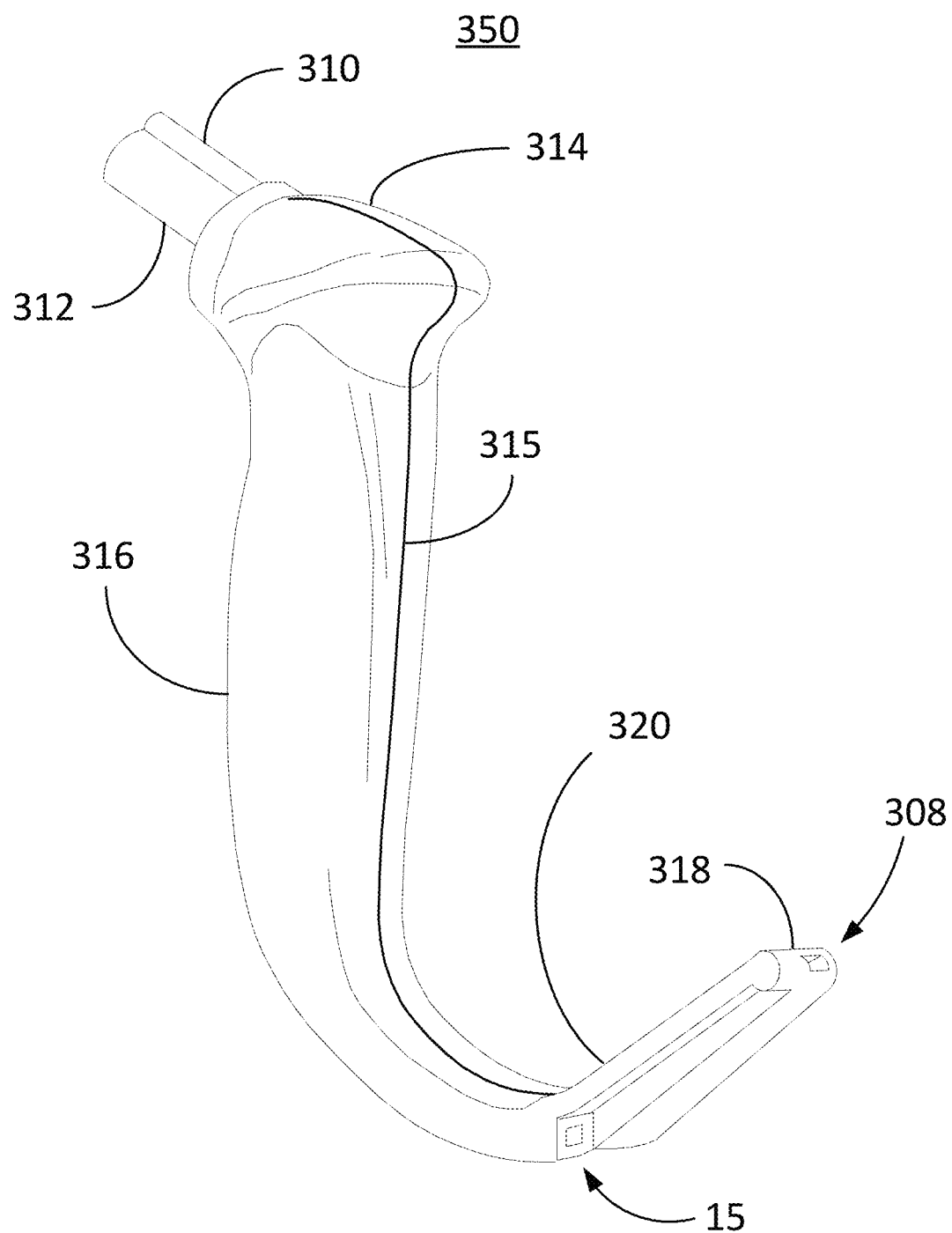
FIG. 8 is a line drawing of an angled view of an optional oxygen dispensing laryngoscope with an exhaust port at the distal end of a laryngoscope blade consistent with embodiments of the present invention.

FIG. 8 is a line drawing of an angled view of an optional oxygen dispensing laryngoscope consistent with embodiments of the present invention. The optional oxygen dispensing laryngoscope 350 generally comprises a handle 316 that extends between a head 314 and a blade 320 like that of FIG. 7A except that the exhaust port 308 is at the blade distal end 318. Specifically, the gas carrying passageway (305, which is not shown in this figure) extends from the entry port (302) in the gas connecting tube 310, through the head 314 and handle 316 all the way to the distal end 318 of the blade 320. For reference the light/camera connecting tube 312 by the head 314 and the light and/or camera 15 is shown in the blade 320. Like the laryngoscope 300, the gas carrying passageway (305) can be molded into or at the seam 315.

FIGS. 9A-9D are line drawings of an oxygen dispensing laryngoscope sleeve used with a laryngoscope consistent with embodiments of the present invention. The present laryngoscope sleeve 400 is envisioned to be a disposable covering that protects a laryngoscope (such as the prior art laryngoscope 10 of FIG. 1) from damage or contamination. The laryngoscope 10 is shaded to provide reference relative to the laryngoscope sleeve 400. As such, certain embodiments contemplate the laryngoscope sleeve 400 being flexible or otherwise having a lower durometer than that of the laryngoscope 10. The laryngoscope sleeve 400 can be made of flexible PVC, silicone, rubber, etc.

Figure 9A:
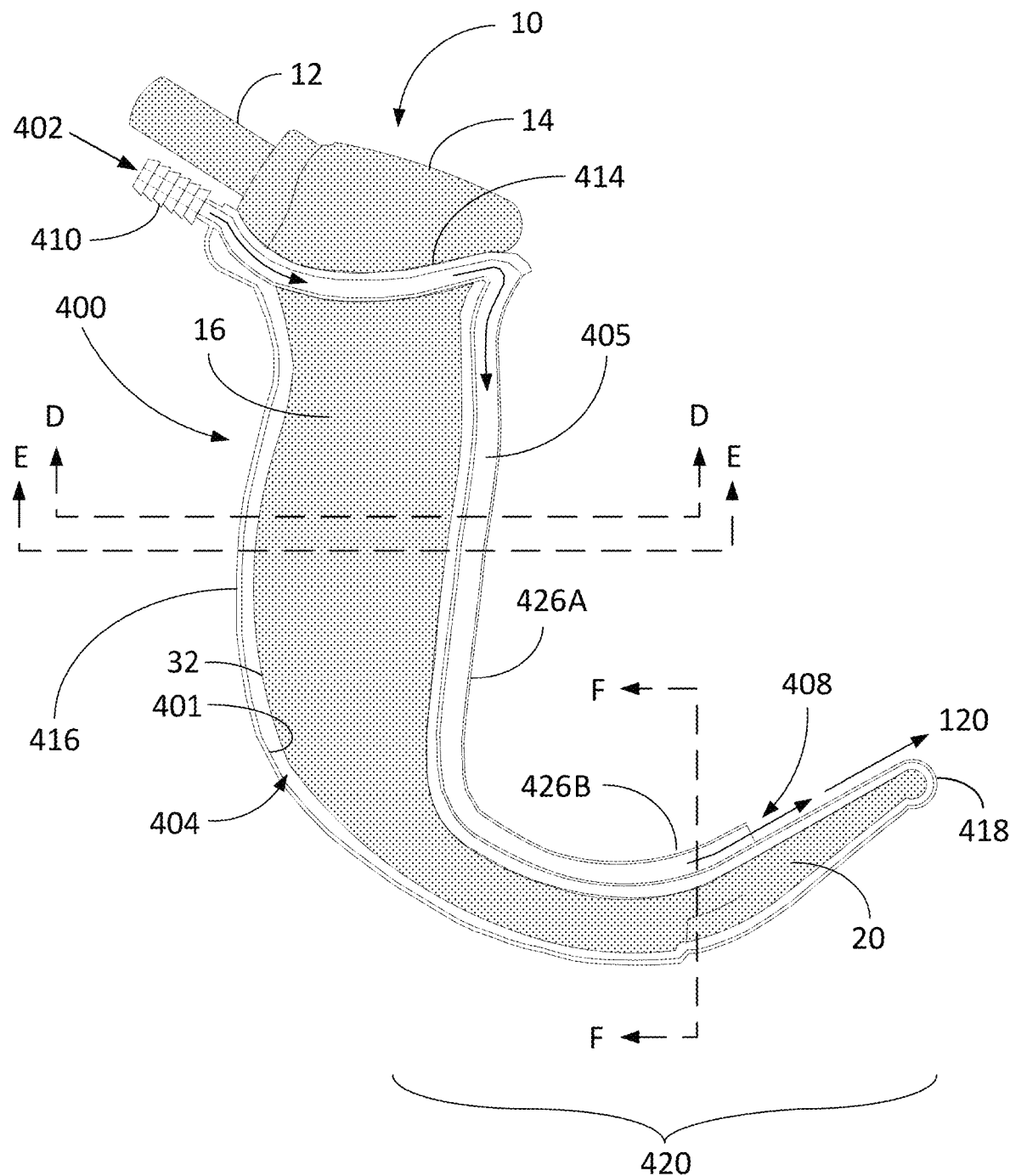
FIGS. 9A-9D are line drawings of an oxygen dispensing laryngoscope sleeve used with a laryngoscope consistent with embodiments of the present invention.

FIG. 9A is a side view of a laryngoscope sleeve 400, which in this depiction is a clear laryngoscope sleeve 400 to provide a better visual of the transparent laryngoscope sleeve 400 conforming to the laryngoscope 10. The laryngoscope sleeve 400 snuggly conforms to the laryngoscope handle 16 and blade 20, as depicted by the clearance gap 404 between the laryngoscope outer surface 32 and the sleeve inner surface 401. The laryngoscope 10 slides into the laryngoscope sleeve 400 via a laryngoscope receiving aperture 414, which is sized and configured to receive the laryngoscope handle 16 and blade 20. In this embodiment, a gas carrying passageway 405 traverses a portion of the laryngoscope receiving aperture 414 just under the head 14 and extends along the sleeve handle 416 to the sleeve blade 420 between the sleeve distal end 418 and the sleeve handle 416. The gas carrying passageway 405 is configured to receive gas 120 in an entry port 402 in a gas connecting tube 410, traverse along a sleeve handle front facing portion 426A of the sleeve handle 416 to an exhaust port 408 in a blade front facing portion 426B. The gas 120 is dispensed from the exhaust port 408 where it is directed over the sleeve distal end 418 to the airway 282 of a patient 280. The gas connecting tube 410 extends from at or approximately at the laryngoscope receiving aperture 414. Some embodiments envision the gas connecting tube 410 extending from the laryngoscope sleeve 400 within a half of an inch from the laryngoscope receiving aperture 414 while other embodiments allow for the gas connecting tube 410 to extend from the laryngoscope sleeve 400 in a location other than near or at the laryngoscope receiving aperture 414. The laryngoscope sleeve 400 is arced in a concave shape like the laryngoscope 10 with a blade front facing portion 426B being in view of a handle front facing portion 426A. The laryngoscope sleeve 400 is sectioned by cross-section cutlines D-D, E-E and F-F.

Figure 9B:
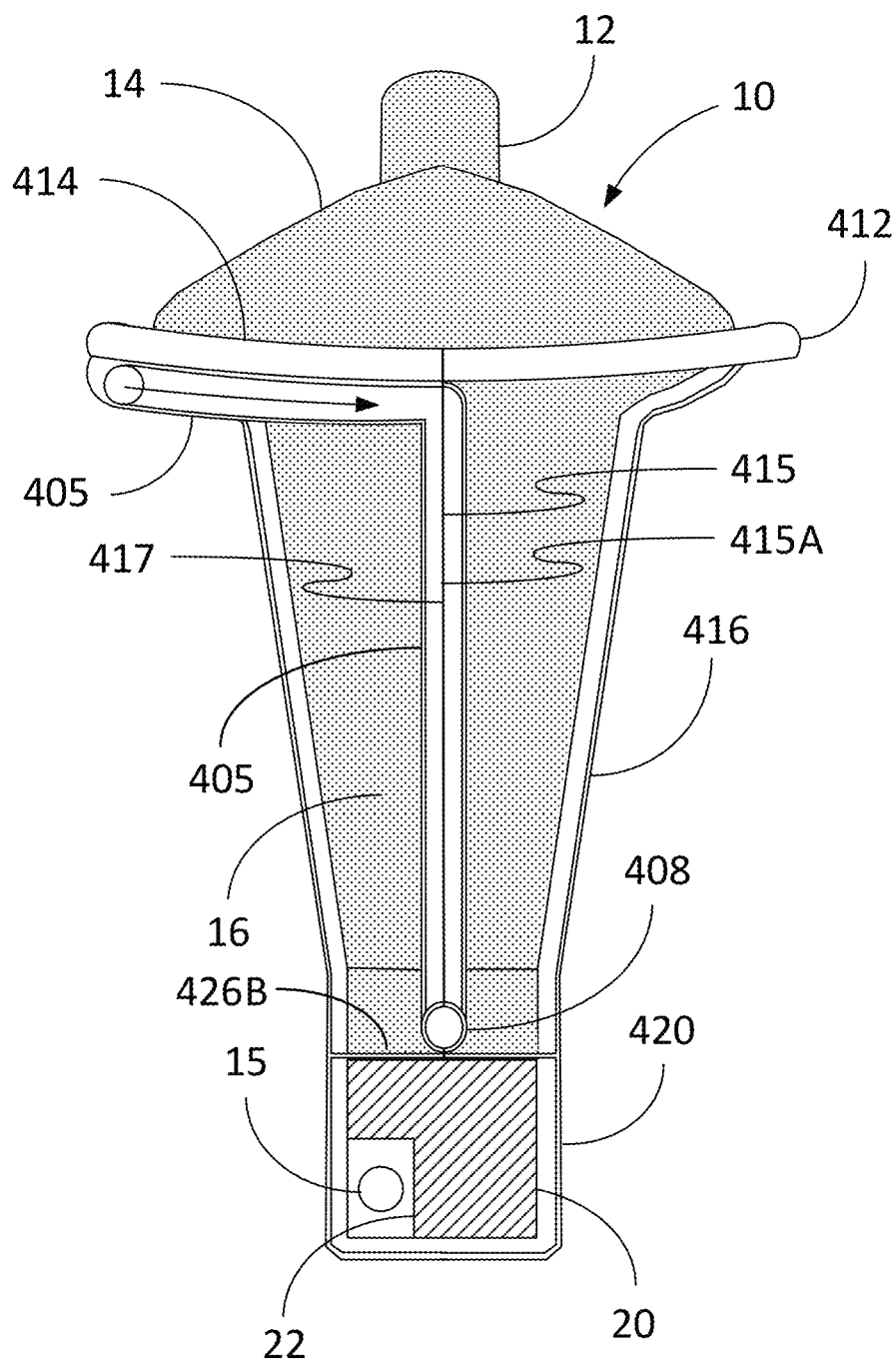

FIG. 9B illustratively depicts a front view of the laryngoscope sleeve 400 covering laryngoscope 20 showing the cross-section F-F of the blade 20 and the sleeve blade 420. The gas carrying passageway 405 traverses a portion of the aperture lip 412 of the laryngoscope receiving aperture 414 to the left side of the centerline 417. The centerline 417 coincides with the seam 415 and the front seam 415A. The cutline F-F is right in front of both the exhaust port 408 and the light and/or camera 15 showing the recess of the camera/light termination location 22. The front seam 415A is depicted extending along the aperture lip 412, the sleeve handle 316 and part of the blade sleeve front facing portion 426B.

Figure 9C:
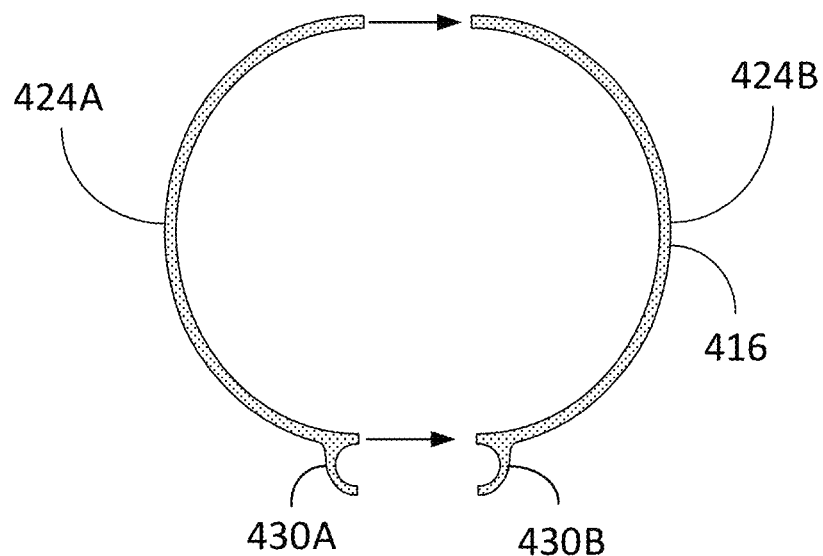
Figure 9D:
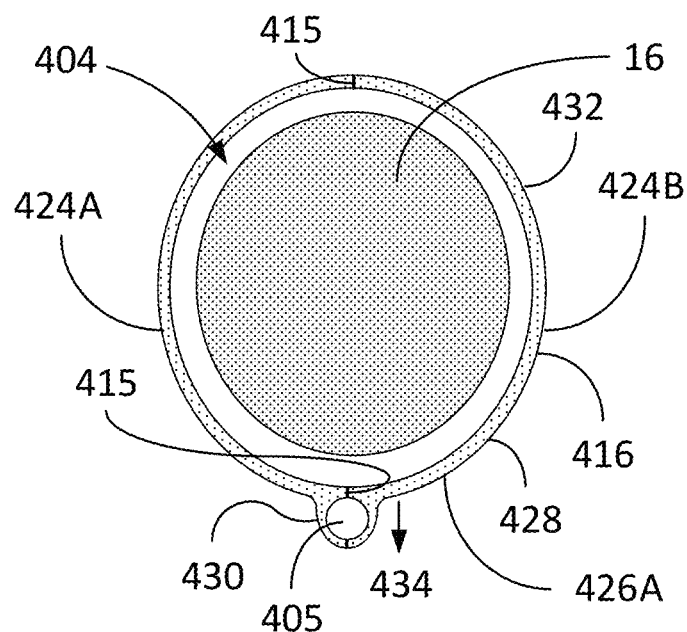

FIGS. 9C and 9D illustratively depict the laryngoscope sleeve 400 at the sleeve handle 416 between the cross-section cutlines D-D and E-E consistent with embodiments of the present invention. As shown in FIG. 9C, one manufacturing method contemplates a first mold (typically a transparent or opaque flexible polymer, such as PCV, for example) of the laryngoscope sleeve left side 424A positioned to be connected to a laryngoscope sleeve right side 424B, as shown by the arrows. In this embodiment, the gas carrying passageway 405 is formed by a first casing portion 430A on the right side and a second casing portion 430B on the left side. FIG. 9D illustratively depicts the cross-section of the handle 16 between the cross-section cutlines D-D and E-E. As shown, the laryngoscope sleeve left side 424A is connected to a laryngoscope sleeve right side 424B with the casing 430 defining the gas carrying passageway 405. The laryngoscope sleeve left side 424A can be connected to a laryngoscope sleeve right side 424B via methods known to those skilled in the art, such as a sonic weld process, heat staking process, glue, bolt, for example. The casing 430 essentially places the gas carrying passageway 405 extending outwardly 434 along the sleeve handle outer surface 432 and the sleeve handle front facing portion 426A. Other embodiments envision the casing 430 residing along the sleeve handle inner surface 401 or somewhere between the handle inner surface 401 and the sleeve handle outer surface 432. The seam 415 is where the laryngoscope sleeve left side 424A and the laryngoscope sleeve right side 424B connect, which is prominently shown by the centerline.

With the present description in mind, below are some examples of certain embodiments illustratively complementing some of the methods and apparatus embodiments discussed above and presented in the figures to aid the reader. The elements called out below are provided by example to assist in the understanding of the present invention and should not be considered limiting. The reader will appreciate that the below elements and configurations can be interchangeable within the scope and spirit of the present invention.

In that light, one inventive aspect of the present invention contemplates a method for oxygenating a patient during intubation, see FIGS. 2A-6. The method comprising providing a tubular laryngoscope comprising a semirigid laryngoscope tube 154 defined between an inlet port 154 and outlet port 152. A handle 102 is connected to the laryngoscope tube 150 at a proximal tube region 158 of the laryngoscope tube 150, the proximal tube region 158 includes the inlet port 155, wherein the inlet port 155 is in communication with an outside environment 140. The method further envisions a step for directing oxygen rich gas 120 from an oxygen source 122 in a flow direction that is through the laryngoscope tube 150 towards the outlet port 152. A first portion of the oxygen rich gas 132 flows in the flow direction through the outlet port 152 while the laryngoscope tube 150 is in a patient airway 282, and a second portion of the oxygen rich gas 120 flows counter to the flow direction through the inlet port 154 and into the outside environment 140.

Another embodiment of the present invention envisions a laryngoscope embodiment 300 comprising a laryngoscope that provides a pathway for gas, such as enriched oxygen 120, to be expelled from a laryngoscope blade 320 to oxygenate a patient 280 when being intubated. The laryngoscope embodiment 300, as shown in FIGS. 7A-7F, can comprise a handle 316 that extends between a head 314 and a blade 320, wherein the laryngoscope 300 has a seam 315 where a laryngoscope left side 324A is bonded to a laryngoscope right side 324B. The laryngoscope 300 further comprises a gas carrying passageway 305 extending inside of the laryngoscope 300. A front seam 315A of the seam 315 comprises a casing 330 that defines the gas carrying passageway 305, wherein prior to assembly of the laryngoscope 300, the laryngoscope left side 324A comprises a first portion 330A of the casing 330 and the laryngoscope right side 324B comprises a second portion 330B of the casing 330, which when bonded forms the seam 315. The gas carrying passageway 305 extends from an entry port 302 located at the head 314 to an exhaust port 308 located at the blade 320.

The laryngoscope embodiment 300 further envisions the gas carrying passageway 305 being within ¼ inch from an outer surface 332 of the handle 316.

The laryngoscope embodiment 300 further contemplates the laryngoscope left side 324A being bonded to the laryngoscope right side 324B via either a sonic weld or heat stake process.

The laryngoscope embodiment 300 further imagines the handle 316 is solid.

The laryngoscope embodiment 300 further considers the exhaust port 308 located on a distal end 318 of the blade 320.

The laryngoscope embodiment 300 further envisions the exhaust port 308 being located on a blade front facing portion 326B of the blade 320 between a blade distal end 318 and the handle 316, wherein the blade front facing portion 326B is in view of a handle front facing portion 326A of the handle 316.

The laryngoscope embodiment 300 further imagines comprising an exhaust port hood 306 that partially covers the exhaust port 308. This embodiment further considers the blade front facing portion 326B to be at least partially concave. This embodiment optionally considers the handle 316 to be hollow and wherein the gas carrying passageway 305 being located along the seam 315 at the handle front facing portion 326A.

The laryngoscope embodiment 300 further envisions the entry port 302 being at a free end of a connecting tube 310 extending from the head 314.

Another embodiment of the present invention envisions a gas dispensing laryngoscope 300 comprising a handle 316 extending between a head 314 and a blade 320 with a gas carrying passageway 305 for dispensing oxygen (or some other gas) during an intubation procedure, as shown in FIGS. 7A-7F. The gas dispensing laryngoscope 300 defines a left side 324A and a right side 324B that are bonded together at a seam 315. The gas dispensing laryngoscope 300 defines a blade front facing portion 326B of the blade 320 and a handle front facing portion 326A of the handle 316, wherein the blade front facing portion 326B is in view of the handle front facing portion 326A. The gas carrying passageway 305 extends inside of the gas dispensing laryngoscope 300 along the seam 315 at the handle front facing portion 326A and the blade front facing portion 326B. The gas carrying passageway 305 extends from an entry port 302 located at the head 314 to an exhaust port 308 located at the blade 320.

The gas dispensing laryngoscope 300 further envisions the handle 316 being solid.

The gas dispensing laryngoscope 300 further imagines the left side 324A of the laryngoscope 300 being bonded to a right side 324B of the laryngoscope 300 via either a sonic weld or heat stake process.

The gas dispensing laryngoscope 300 further contemplates the exhaust port 308 being located on the blade front facing portion 326B between a blade distal end 318 and the handle 316. The gas dispensing laryngoscope 300 could further comprise an exhaust port hood 306 that partially covers the exhaust port 308.

The gas dispensing laryngoscope 300 further envisions the exhaust port 308 being located on a distal end 318 of the blade 320.

The gas dispensing laryngoscope 300 is further contemplated to have the gas carrying passageway 305 being located along the seam 315 where the seam 315 extends along the blade front facing portion 326B and the handle front facing portion 326A.

Still another embodiment of the present invention envisions a laryngoscope 300 that channels gas during an intubation, which provides an example shown in FIGS. 7A-7F. The laryngoscope 300 can comprise a handle 316 extending between a head 314 and a blade 320, wherein the blade 320 has a blade front facing portion 326B and the handle 316 has a handle front facing portion 326A. The blade front facing portion 326B is in view of the handle front facing portion 326A. The laryngoscope 300 defines a left side 324A and a right side 324B that at least in part meet along a centerline 317 at the handle front facing portion 326A and the blade front facing portion 326B. The laryngoscope 300 further comprises a gas carrying passageway 305 that extends inside of the gas dispensing laryngoscope 300 along the centerline 317 at the handle front facing portion 326A and the blade front facing portion 326B. The gas carrying passageway 305 extends from an entry port 302, that is located at the head 314, to an exhaust port 308, that is located at the blade 320.

An embodiment of the laryngoscope 300 further envisions the centerline 317 being a molded seam 315 established by either a sonic weld process or heat stake process.

This laryngoscope embodiment 300 further imagines that the handle 316 is hollow and the gas carrying passageway 305 is located at the seam 315 that extends along the handle front facing portion 326A.

Another embodiment of the present invention contemplates a laryngoscope sleeve 400 configured to cover a substantial portion of a laryngoscope 10, wherein the laryngoscope sleeve 400 is configured to dispense gas 120, such as enriched oxygen, to a patient 280 in need of air as exemplified in FIGS. 9A-9D. The laryngoscope sleeve 400 can comprise a sleeve handle 416 that extends between a laryngoscope receiving aperture 414 and a sleeve blade 420, wherein laryngoscope sleeve 400 comprises a sleeve seam 415 where a left side 424A of the laryngoscope sleeve 400 is bonded to a right side 424B of the laryngoscope sleeve 400. A front seam 415A is located along a blade front facing portion 426B of the sleeve blade 420 and a handle front facing portion 426A of the sleeve handle 416, wherein the blade front facing portion 426B is in view of the handle front facing portion 426A. The front seam 415A comprises a casing 430 that defines a gas carrying passageway 405, wherein the left side 424A comprises a first passageway portion 405A of the left casing portion 430A and the right side 424B comprises a second passageway portion 405B of the right casing portion 430B. The gas carrying passageway 405 extends from an entry port 402 located at the laryngoscope receiving aperture 414 to an exhaust port 408 located at the sleeve blade 420.

An embodiment of the laryngoscope sleeve 400 further envisions the left side 424A of the laryngoscope sleeve 400 being bonded to a right side 424B of the laryngoscope sleeve 400.

The laryngoscope sleeve embodiment 400 further imagines the left side 424A of the laryngoscope sleeve 400 being bonded to a right side 424B of the laryngoscope sleeve 400 via either a sonic weld or heat stake process.

An embodiment of the laryngoscope sleeve 400 further envisions the laryngoscope sleeve 400 substantially conforming to the shape of a laryngoscope 10 with a clearance gap 404 between a laryngoscope outer surface 32 of the laryngoscope 10 and the inner surface 401 of the laryngoscope sleeve 400.

The laryngoscope sleeve embodiment 400 further contemplates the exhaust port 408 being located on a distal end 418 of the sleeve blade 420.

An embodiment of the laryngoscope sleeve 400 further imagines the exhaust port 408 being located on a blade front facing portion 426B of the sleeve blade 420 between a blade distal end 418 and the sleeve handle 416, wherein the blade front facing portion 426B is in view of a handle front facing portion 426A of the sleeve handle 416.

The laryngoscope sleeve embodiment 400 further considers the casing 430 extending outwardly 434 from a primary sleeve handle shape 428 of the sleeve handle 416.

An embodiment of the laryngoscope sleeve 400 further envisions the laryngoscope receiving aperture 414 being adapted to receive a laryngoscope 10.

The laryngoscope sleeve embodiment 400 further imagines comprising a gas connecting tube 410 that extends from the laryngoscope sleeve 400, wherein the sleeve connecting tube 410 comprises the entry port 402 at a free end of the sleeve connecting tube 410, which is in communication with the gas carrying passageway 405. Additionally, the gas connecting tube 410 can be located essentially at the laryngoscope receiving aperture 414.

Still another embodiment of the present invention envisions a gas dispensing laryngoscope sleeve 400, as exemplified in FIGS. 9A-9D, comprising a sleeve handle 416 extending between a laryngoscope receiving aperture 414 and a sleeve blade 420 that facilitates dispensing gas 120, such an oxygen, to a patient 280 in breathing distress. The gas dispensing laryngoscope sleeve 400 defines a left side 424A and a right side 424B bonded together at seam 415. The gas dispensing laryngoscope sleeve 400 further defines a blade front facing portion 426B of the sleeve blade 420 and a handle front facing portion 426A of the sleeve handle 416, wherein the blade front facing portion 426B is in view of the handle front facing portion 426A. A gas carrying passageway 405 extends outside of the gas dispensing laryngoscope sleeve 400 along the seam 415 at the handle front facing portion 426A and the blade front facing portion 426B from an entry port 402 to an exhaust port 408 located at the sleeve blade 420. The entry port 402 is located at a free end of a gas connecting tube 410 approximately at the laryngoscope receiving aperture 414.

An embodiment of the gas dispensing laryngoscope sleeve 400 further envisions the gas carrying passageway 405 being defined within a casing 430 that extends along a front seam 415A of the seam 415, wherein the left side 424A comprises a first passageway portion 405A of the left casing portion 430A and the right side 424B comprises a second passageway portion 405B of the right casing portion 430B. Furthermore, the left side 424A of the laryngoscope sleeve 400 could be bonded to a right side 424B of the laryngoscope sleeve 400 via either a sonic weld or heat stake process. In an optional embodiment, the casing 430 can extend outwardly 434 from a primary sleeve handle shape 428 of the sleeve handle 416.

Another embodiment of the gas dispensing laryngoscope sleeve 400 further imagines the exhaust port 408 being located on the blade front facing portion 426B between a sleeve blade distal end 418 of the sleeve blade 420 and the sleeve handle 416.

The gas dispensing laryngoscope sleeve embodiment 400 further contemplates the laryngoscope receiving aperture 414 being adapted to receive a laryngoscope 10.

Another embodiment of a laryngoscope sleeve 400 that channels gas 120, such as enriched oxygen, to a patient 280 in need of air as exemplified in FIGS. 9A-9D, envisions a sleeve handle 416 extending between a laryngoscope receiving aperture 414 and a sleeve blade 420 with a gas emitting port 308. The laryngoscope sleeve 400 defines a blade front facing portion 426B of the sleeve blade 420 and a handle front facing portion 426A of the sleeve handle 416, wherein the blade front facing portion 426B is in view of the handle front facing portion 426A. The laryngoscope sleeve 400 defines a left side 424A and a right side 424B that at least in part meet along a centerline 417 at the handle front facing portion 426A and the blade front facing portion 426B. A gas carrying passageway 405 extends along the centerline 417 at the handle front facing portion 426A and the blade front facing portion 426B from an entry port 402, located at a distal end of a gas connecting tube 410, to an exhaust port 408 located at the sleeve blade 420.

The laryngoscope sleeve 400 further imagines the centerline 417 being a molded seam 415 established or otherwise formed by either a sonic weld process or heat stake process.

The laryngoscope sleeve 400 further contemplates the gas carrying passageway 405 being defined within a casing 430 that extends along a front seam 415A of the seam 415, wherein the left side 424A comprises a first portion 405A of the left casing portion 430A, which could be a first half of the laryngoscope sleeve 400 and the right side 424B comprises a second portion 405B of the right casing portion 430B.

The laryngoscope sleeve 400 further considers the laryngoscope receiving aperture 414 being adapted to receive a laryngoscope 10.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe a laryngoscope tube 150 and a laryngoscope blade 260 other similar devices can be used with oxygen sources to provide a flow of oxygen into a patient's lungs while being or during the process of being intubated. It should also be appreciated that the appropriate components not discussed in detail in the present disclosure must be implemented in accordance known to those skilled in the art. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A laryngoscope sleeve comprising:
   a sleeve handle that extends between a laryngoscope receiving aperture and a sleeve blade, wherein the laryngoscope sleeve comprises a sleeve seam where a left side of the laryngoscope sleeve is bonded to a right side of the laryngoscope sleeve;
   a front seam located along a blade front facing portion of the sleeve blade and a handle front facing portion of the sleeve handle, the blade front facing portion is in view of the handle front facing portion;
   the front seam comprising a casing that defines a gas carrying passageway, wherein the left side comprises a first portion of the casing and the right side comprises a second portion of the casing; and the gas carrying passageway extending from an entry port located at the laryngoscope receiving aperture to an exhaust port located at the sleeve blade.

2. The laryngoscope sleeve of claim 1, wherein the left side of the laryngoscope sleeve is bonded to the right side of the laryngoscope sleeve via either a sonic weld or heat stake process.

3. The laryngoscope sleeve of claim 1, wherein the laryngoscope sleeve substantially conforms to the shape of a laryngoscope with a clearance gap between a laryngoscope outer surface of the laryngoscope and an inner surface of the laryngoscope sleeve.

4. The laryngoscope sleeve of claim 1, wherein the exhaust port is located on a distal end of the sleeve blade.

5. The laryngoscope sleeve of claim 1, wherein the exhaust port is located on the blade front facing portion portion of the sleeve blade between a blade distal end and the sleeve handle.

6. The laryngoscope sleeve of claim 1, wherein the casing extends outwardly from a primary sleeve handle shape of the sleeve handle.

7. The laryngoscope sleeve of claim 1, wherein the laryngoscope receiving aperture is adapted to receive a laryngoscope.

8. The laryngoscope sleeve of claim 1 further comprising a gas connecting tube that extends from the laryngoscope sleeve, the gas connecting tube comprises the entry port at a free end of the gas connecting tube, which is in communication with the gas carrying passageway.

9. The laryngoscope sleeve of claim 8, wherein the gas connecting tube is located essentially at the laryngoscope receiving aperture.

10. A gas dispensing laryngoscope sleeve comprising:
a sleeve handle extending between a laryngoscope receiving aperture and a sleeve blade,
the gas dispensing laryngoscope sleeve defining a left side and a right side bonded together at a seam;
the gas dispensing laryngoscope sleeve defining a blade front facing portion of the sleeve blade and a handle front facing portion of the sleeve handle, wherein the blade front facing portion is in view of the handle front facing portion;
a gas carrying passageway extending outside of the gas dispensing laryngoscope sleeve along the seam at the handle front facing portion and the blade front facing portion; and
the gas carrying passageway extending from an entry port to an exhaust port located at the blade,
the entry port is located at a free end of a gas connecting tube,
the entry port located approximately at the laryngoscope receiving aperture.

11. The gas dispensing laryngoscope sleeve of claim 10, wherein the gas carrying passageway is defined within a casing that extends along a front seam of the seam, the left side comprises a first portion of the casing and the right side comprises a second portion of the casing.

12. The gas dispensing laryngoscope sleeve of claim 11, wherein the left side of the laryngoscope sleeve is bonded to the right side of the laryngoscope sleeve via either a sonic weld or heat stake process.

13. The gas dispensing laryngoscope sleeve of claim 11, wherein the casing extends outwardly from a primary sleeve handle shape of the sleeve handle.

14. The gas dispensing laryngoscope sleeve of claim 10, wherein the exhaust port is located on the blade front facing portion between a sleeve blade distal end of the sleeve blade and the sleeve handle.

15. The gas dispensing laryngoscope sleeve of claim 10, wherein the laryngoscope receiving aperture is adapted to receive a laryngoscope.

16. A laryngoscope sleeve that channels gas, the laryngoscope sleeve comprising:
a sleeve handle extending between a laryngoscope receiving aperture and a sleeve blade, the laryngoscope sleeve defining a blade front facing portion of the sleeve blade and a handle front facing portion of the sleeve handle, wherein the blade front facing portion is in view of the handle front facing portion;
the laryngoscope sleeve defining a left side and a right side that at least in part meet along a centerline at the handle front facing portion and the blade front facing portion;
a gas carrying passageway extending along the centerline at the handle front facing portion and the blade front facing portion; and
the gas carrying passageway extending from an entry port, located at a distal end of a gas connecting tube, to an exhaust port located at the sleeve blade.

17. The laryngoscope sleeve of claim 16, wherein the centerline is a molded seam established by either a sonic weld process or heat stake process.

18. The laryngoscope sleeve of claim 16, wherein the gas carrying passageway is defined within a casing that extends along a front seam of the seam, the left side comprises a first portion of the casing and the right side comprises a second portion of the casing.

19. The laryngoscope sleeve of claim 16, wherein the laryngoscope receiving aperture is adapted to receive a laryngoscope.

* * * * *